United States Patent
Miyazaki

[19]
[11] Patent Number: 5,892,139
[45] Date of Patent: Apr. 6, 1999

[54] ROAD SURFACE FRICTION SENSOR AND COEFFICIENT DETECTOR

[75] Inventor: Nagao Miyazaki, Osaka, Japan

[73] Assignee: Japan Electronics Industry, Limited, Osaka, Japan

[21] Appl. No.: 980,185

[22] Filed: Nov. 26, 1997

Related U.S. Application Data

[63] Continuation of Ser. No. 731,101, Oct. 9, 1996, abandoned, which is a continuation of Ser. No. 512,051, Aug. 7, 1995, abandoned, which is a continuation of Ser. No. 277,941, Jul. 20, 1994, abandoned, which is a continuation of Ser. No. 832,634, Feb. 7, 1992, abandoned, which is a continuation of Ser. No. 514,457, Apr. 25, 1990, abandoned, which is a division of Ser. No. 370,224, Jun. 22, 1989, abandoned.

[30] Foreign Application Priority Data

| Oct. 13, 1988 | [JP] | Japan | 63-259224 |
| Oct. 13, 1988 | [JP] | Japan | 63-259225 |
| Oct. 13, 1988 | [JP] | Japan | 63-259226 |
| Feb. 23, 1989 | [JP] | Japan | 1-44537 |

[51] Int. Cl.$^6$ ............................ G01N 19/02
[52] U.S. Cl. ............................ 73/9; 73/146
[58] Field of Search ............ 73/9, 10, 105, 73/146; 180/147; 303/149, 150; 701/70, 73, 80

[56] References Cited

U.S. PATENT DOCUMENTS

| 2,700,297 | 1/1955 | Allen | 73/9 |
| 3,033,018 | 5/1962 | Haggadone | 73/9 |
| 3,711,162 | 1/1973 | Steinbrenner et al. | |
| 4,315,426 | 2/1982 | Brandon | 73/9 |
| 4,662,211 | 5/1987 | Strong | 73/9 |
| 4,666,218 | 5/1987 | Masaki et al. | 324/426.02 X |
| 4,779,447 | 10/1988 | Rath | 73/9 |
| 4,866,982 | 9/1989 | Gault | 73/745 X |
| 4,882,693 | 11/1989 | Yopp | 73/9 X |
| 4,955,933 | 9/1990 | Sistonen | 73/9 |
| 4,958,512 | 9/1990 | Johnsen | 73/9 |
| 4,986,118 | 1/1991 | Pottinger | 73/146 |
| 4,997,202 | 3/1991 | Kitagawa et al. | 364/562 X |

FOREIGN PATENT DOCUMENTS

| 228834 | 8/1963 | Austria | 73/146 |
| 2.145.532 | 2/1973 | France . | |
| 2647505 | 1/1978 | Germany | 73/146 |
| 3226074A1 | 9/1983 | Germany . | |
| 47-39904 | 10/1972 | Japan | 73/9 |
| 55-46150 | 3/1980 | Japan | 73/9 |
| 56-39946 | 4/1981 | Japan . | |
| 62-110554 | 5/1987 | Japan . | |
| 568859 | 11/1977 | U.S.S.R. | 73/146 |
| 582469 | 11/1977 | U.S.S.R. | 73/146 |
| 2121495 | 12/1983 | United Kingdom . | |

OTHER PUBLICATIONS

*Patent Abstracts of Japan*: Grp. M074, vol. 5, No. 93; ABS pub. dat Jun. 17, 1981 (56–39946).

"Automatic Electrical Measurement of Contact Pressure Distribution of a Spherical Wheel Running on Soft Powdery Ground"; *Japanese Journal of Applied Physics*; vol. 21, No. 6, pp. 940–943, Jun. 1982; in 73/146 Kiyoshi Takahashi et al.

*Patent Abstract of Japan*; Grp. M 404, vol. 9, No. 198; ABS pub. date Aug. 15, 1985 (60–61354).

*Patent Abstracts of Japan*: Grp M765, vol. 12, No. 437; ABS pub. date Nov. 17, 1988 (63–170157).

*Primary Examiner*—Thomas P. Noland
*Attorney, Agent, or Firm*—Jordan and Hamburg LLP

[57] ABSTRACT

Road surface friction is sensed by measuring strain on a structure of a vehicle in the vicinity of a wheel of the vehicle. Road surface friction coefficient is determined by measuring strain on a structure of a vehicle in the vicinity of a wheel of the vehicle thereby to produce signal outputs proportional to road surface frictional force and vertical load and calculating the road surface friction coefficient from the outputs.

4 Claims, 20 Drawing Sheets

ROAD SURFACE FRICTION SENSOR AND COEFFICIENT DETECTOR

This application is a continuation of application Ser. No. 08/731,101, filed Oct. 9, 1996, now abandoned, which is a continuation of application Ser. No. 08/512,051, filed Aug. 7, 1995, now abandoned, which is a continuation of application Ser. No. 08/277,941, filed Jul. 20, 1994, now abandoned, which is a continuation of application Ser. No. 07/832,634, filed Feb. 7, 1992, now abandoned, which is a continuation of application Ser. No. 07/514,457, filed Apr. 25, 1990, now abandoned, which is a division of application Ser. No. 07/370,224, filed Jun. 22, 1989, now abandoned.

BACKGROUND OF THE INVENTION

Technical Field

This invention relates to an antilock braking device for precluding the locking of the wheels of a vehicle on sudden application of the brake and a road surface friction sensor and a road surface friction coefficient detector which can be used as components of the antilock braking device.

Technical Background

The conventional antilock braking device for cars or other vehicles generally employs a system such that the braking action is automatically controlled according to the chassis speed and wheel speed in such a manner that the slip ratio will fall within a definite range (see, for example, Japanese Patent Publication No. 30585/1984 and Japanese laid-open Patent Application KOKAI No. 61354/1985). The relationship between road surface friction coefficient and slip ratio is variable according to the texture of the road surface and, for this reason, the above system does not always provide the maximum braking force, depending on the condition of the road surface, and, in such cases, does not insure the minimum braking distance. Furthermore, because the chassis speed value used is an approximate value estimated from the wheel speed, the precision of slip ratio control is not sufficiently high. In order to ascertain the exact chassis speed, one has to rely on complicated devices such as a ground relative speed sensor (for example, Japanese laid-open Patent Application No. 64861/1988) or chassis deceleration sensor (for example, Japanese laid-open Patent Application No. 170157/1988).

In the conventional antilock braking device described in Japanese laid-open Patent Application No. 25169/1988, the road surface friction torque acting on the wheel (tire torque) is calculated from the wheel angular acceleration and brake fluid pressure values and the beginning of a fall in tire torque during the elevation of brake fluid pressure is utilized as one of the criteria for ascertaining the condition immediately preceding a wheel lock. However, since the tire torque is indirectly calculated from the wheel angular acceleration and brake fluid pressure, the above system does not take care of indefinite constants such as the moment of inertia of the wheels, the braking efficiency of the brake and so on, thus presenting problems in terms of the accuracy of data. There also is the problem that since the distance from the wheel to the road surface varies according to the deceleration of the chassis, depending on the pneumatic pressure of the tires and the weight of the chassis, the road surface friction force and the tire torque are not necessarily maintained in a fixed ratio.

It is an object of this invention to provide an antilock braking device free from the above-mentioned disadvantages of the conventional device.

It is another object to provide a road surface frictional force sensor and a road surface friction coefficient detector which can be used as components of an antilock braking device.

SUMMARY OF THE INVENTION

A first antilock braking device according to this invention includes a brake control means adapted to cyclically perform an operational series which comprises sensing the road surface frictional force, increasing the brake fluid pressure while the road surface frictional force is increasing in response to the elevation of brake fluid pressure, decreasing the brake fluid pressure when the road surface frictional force declines despite elevation of the brake fluid pressure, and increasing the brake fluid pressure again when the road surface frictional force decreases in response to a fall-off of brake fluid pressure. The road surface frictional force is determinable from measured values of the strain on a vehicle structure in the vicinity of the wheel of the vehicle. Herein the phrase "a vehicle structure in the vicinity of the wheel of a vehicle" refers to a knuckle of a suspension, an axle housing or the like.

A second antilock braking device according to this invention includes a brake control means adapted to cyclically perform an operational series which comprises detecting the coefficient of road surface friction, increasing the brake fluid pressure while the road surface friction coefficient is increasing in response to the elevation of brake fluid pressure, relieving or releasing the brake fluid pressure as the velocity of gain i.e., rate of increase in road surface friction coefficient falls below a set value and increasing the brake fluid pressure again after the road surface friction coefficient has declined below a set value. The road surface friction coefficient value used in this second antilock braking device can be calculated from the road surface frictional force value and the vertical load value obtainable from measured values of the strain on a vehicle structure in the vicinity of the wheel.

The relationship between wheel-road surface slip ratio and road surface friction coefficient can be represented by curves such as shown in FIG. 1. On the ordinary road surface, this relation can be expressed by a curve having a peak as shown at C1. On an extraordinary road surface, such as a snow-clad road surface, the relation may be represented by a curve without a peak as shown at C2. Not only the presence or absence of a peak but also the height of the peak and the magnitude of the slip ratio corresponding to the peak vary with the condition of the road surface and the chassis speed. On the other hand, as represented by curve C3, the cornering force (lateral drag) decreases continuously in response to an increase in slip ratio. Therefore, as far as trackless vehicles such as automobiles are concerned, in order to obtain the maximum braking force without sacrificing the cornering force, it is ideal to apply the brake in the neighborhood of P1 or P2 on curve C1 or C2 as the case may be.

Let it be supposed that the vehicle is running on a road surface such that the relation between road surface friction coefficient and slip ratio can be represented by the curve C1 shown in FIG. 1. It should be understood that the road surface friction force is approximately proportional to the road surface friction coefficient. Under these conditions, the first antilock braking device according to this invention functions as follows. First, as sudden braking is applied by depressing the brake pedal or manipulating the brake lever, the brake fluid pressure increases. While the detected road surface frictional force value continues to rise, the brake fluid pressure is increased consistently to apply the brake with an increasing force. This phase corresponds to the segment to the left of P1 on the curve C1 shown in FIG. 1. As the brake fluid pressure is increased to apply the brake more forcefully, the slip ratio increases to approach the point P1 of maximum road surface friction coefficient. As the brake fluid pressure is further increased, the point P1 is passed over in due course. Beyond P1, locking of the wheels begins to occur as the road surface frictional force begins to decline in response to the elevation of brake fluid pressure. When the road surface friction sensor output decreases in this manner, the brake fluid pressure is decreased to relieve the brake action. Therefore, locking of the wheels is prevented. As the road surface frictional force decreases in response to a decline in brake fluid pressure, the brake fluid pressure is increased again. As the result of this action, as long as the vehicle runs on a road surface which can be represented by a curve with a peak in regard to the road surface friction coefficient-slip ratio relation, the locking of the wheels can be prevented irrespective of road condition and, moreover, braking action making the most of road surface frictional force can be realized.

The frictional force which acts between each wheel of the vehicle and the road surface is dynamically equivalent to the braking force applied by the wheel on the chassis. Therefore, strains and stresses proportional to the road surface frictional force are generated in all given positions of the structure between the point of contact of the wheel with the road surface and the chassis. Therefore, it is possible for one to measure the structural strain at an appropriate point of the structure and detect the road surface frictional force through the strain value. The member of the structure in which the maximum strain is generated is the tire in case the vehicle has tires on its wheels. Therefore, the road surface frictional force can be detected from measured values of the tire strain. It is also possible to affix strain gauges to the bearing shaft supporting the wheel, for instance, and thereby measure the strain on a vehicle structure in the vicinity of the wheel. This strain is smaller than the tire strain but since said shaft is not a rotary element, the construction of the road surface friction sensor can be simplified.

The vertical drag exerted by the road surface on each wheel, or the vertical load which the wheel applies to the road surface as a reaction thereto, can, for the same reason as above, also be detected from a measured value of the strain on a vehicle structure in the vicinity of the wheel.

The second antilock braking device according to this invention functions as follows. As the motorist depresses the brake pedal or manipulates the brake lever with a great force, the antilock braking device is started. In the segment to the left of P1 or P2 on curve C1 or C2, the road surface friction coefficient $\mu$ increases in response to an elevation of brake fluid pressure. However, when the velocity of gain in $\mu$ falls off below a predetermined reference level (slightly to the left of the point P1 or at the point P2), the brake fluid pressure is relieved or released, whereupon the value of $\mu$ begins to diminish. After a decline corresponding to a given proportion of the maximum value immediately preceding the beginning of decrease of the road surface friction coefficient $\mu$, the brake fluid pressure begins to rise again. Thereafter, the above sequence of events is repeated. In this manner, not only when the vehicle is running on a road surface such that the relation between road surface friction coefficient and slip ratio traces the aforementioned curve C1 but also when the road surface can be represented by curve C2 without a peak, the road surface friction coefficient at application of the brake is maintained in the neighborhood of P1 and P2, thus insuring a more or less ideal braking action. For vehicles (rolling stock, etc,) which run on tracks, in which no cornering force is required, said predetermined reference value for the velocity of gain in $\mu$ is set at zero or an appropriate negative value. Then, braking action utilizing the maximum road surface friction force can be insured. The road surface friction coefficient value to be used in this second antilock braking device can be found by computation from the above-mentioned road surface frictional force value and the vertical load values can be obtained from data of strain on a vehicle structure in the vicinity of the wheel.

Thus, according to the device of this invention, the braking distance can be minimized irrespective of the condition of the road surface and, at the same time, the object of an antilock braking effect can be accomplished. Furthermore, the device does not require a complicated setup for measuring the chassis speed.

DETAILED DESCRIPTION OF THE PREFERRED EMBODIMENTS

In the following description of embodiments, an automobile will be taken as an example. However, it should be understood that the present invention is applicable to other types of vehicles as well.

Figure 2:
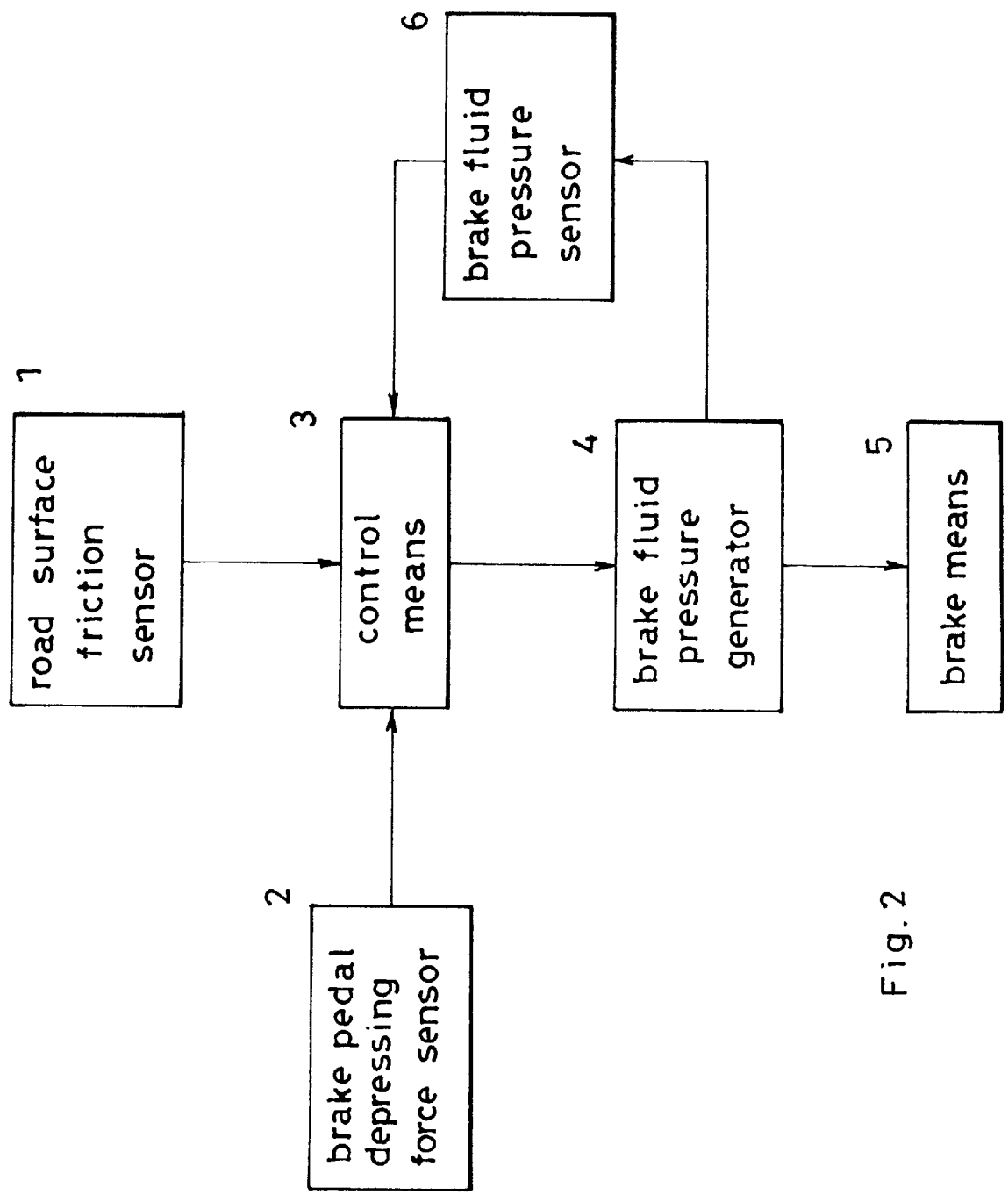
FIG. 2 is a block diagram of the antilock braking device according to an embodiment of this invention.
Figure 3:
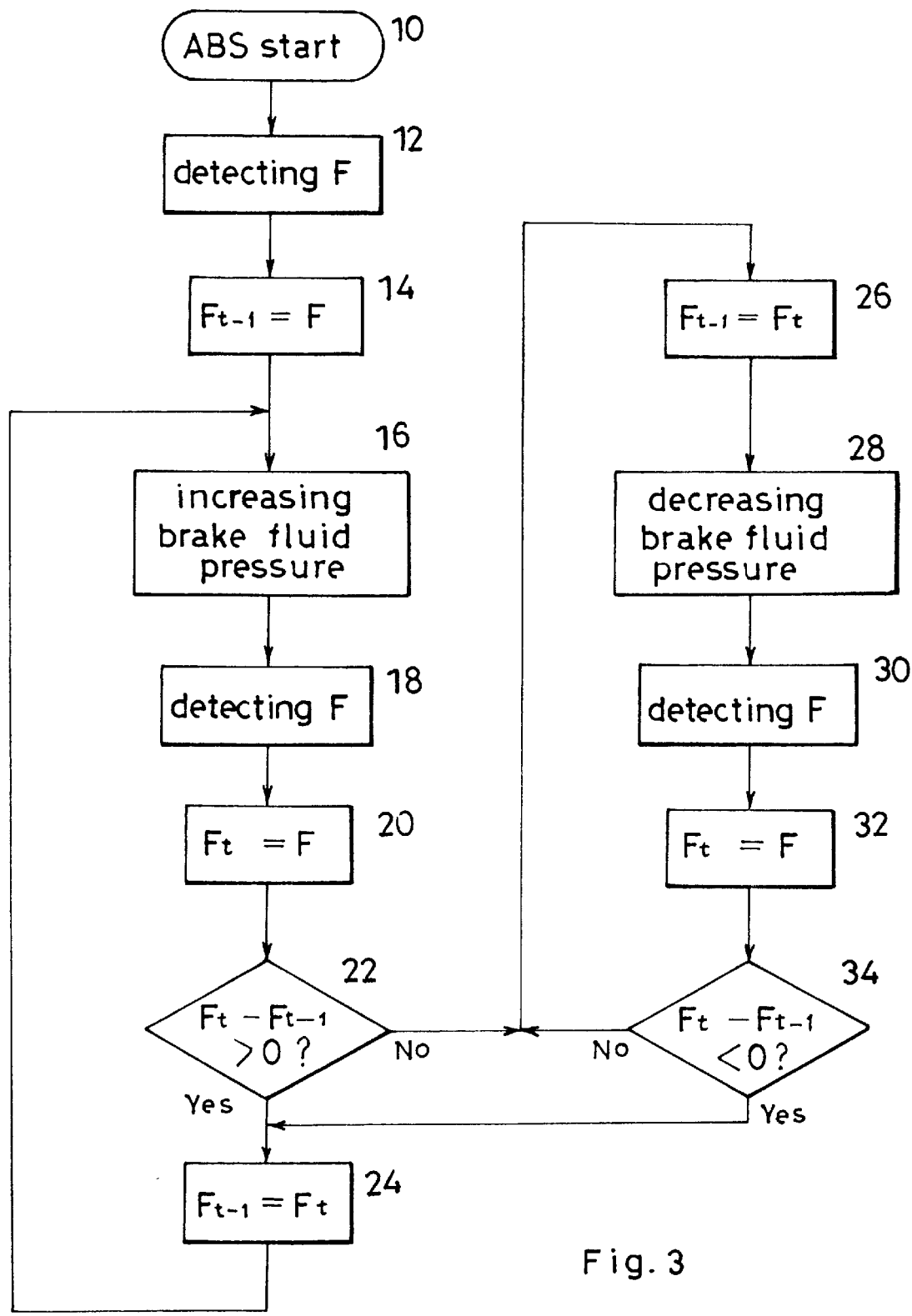
FIG. 3 is a flow chart showing the execution of the program routine in the control means built into the antilock braking device illustrated in FIG. 2.

FIGS. 2 and 3 illustrate an antilock braking device embodying the principle of this invention.

The control means 3 controls the pressure of brake fluid with reference to measured values of brake pedal depressing force, road surface frictional force and brake fluid pressure. A brake pedal depressing force sensor 2, brake fluid pressure generator 4, brake means 5 and brake fluid pressure sensor 6 may each be implemented by utilizing the known technologies. The control means 3 comprises an electronic circuit including a microprocessor, a memory and an input-output interface and functions according to a program written into the memory. An example of the action of this control means 3 is illustrated in the flow chart of FIG. 3. When the brake pedal-depressing force exceeds a set value, the antilock braking device of this invention is started to make a transition from the ordinary braking action to the antilock braking action. Referring to the flow chart of FIG. 3, step 10 represents the beginning of the antilock braking action. Subsequently at step 12, the road surface frictional force F is detected, and at step 14, the above value is stored in a variable $F_{t-1}$. Then, at step 16, the brake fluid pressure is increased. Further at step 18 the road surface frictional force F is detected, and at step 20 this road surface frictional force value is stored in a variable $F_t$. Then, at step 22, it is determined whether the difference between the two variables $F_t$ and $F_{t-1}$, viz. $F_t-F_{t-1}$, is positive or negative. If it is positive, the stored value of variable $F_{t-1}$ is updated to the value of variable $F_t$ at step 24. Then, the sequence returns to step 16. If the difference determined at step 22 is not positive, the sequence proceeds to step 26. At step 26, just as at step 24, the stored value of variable $F_{t-1}$ is updated to the value of variable $F_t$. Then, at step 28, the brake fluid pressure is decreased. Thereafter, the road surface frictional force F is detected at step 30 and this value is stored in variable $F_t$ at step 32. Subsequently, at step 34, as at step 22, the difference $F_t-F_{t-1}$ is determined. If the difference is negative, the sequence proceeds to step 24. If the difference determined at step 34 is not negative, the sequence returns to step 26.

Figure 1:
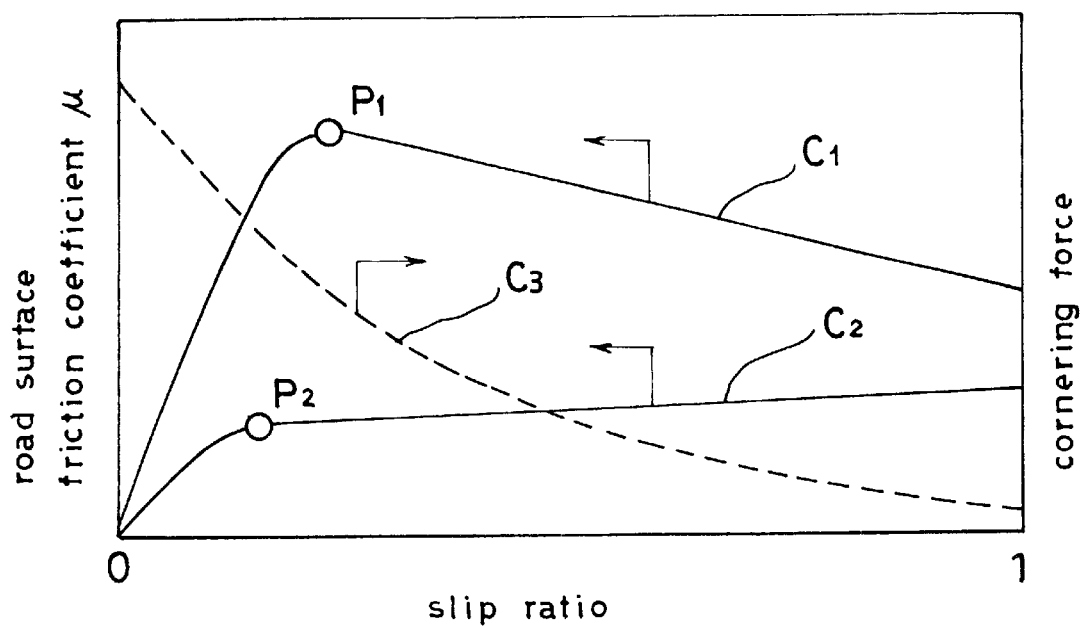
FIG. 1 is a diagrammatic representation of the relationship among slip ratio, road surface friction coefficient and cornering force.

As the control means 3 executes the above program, the brake fluid pressure is controlled in such a manner that the brake will always be applied at or near the maximum road surface friction coefficient (P1 on curve C1 in FIG. 1) irrespective of the condition of the road surface.

However, the above embodiment has the following drawbacks (1) through (4).

(1) The antilock braking device according to the above embodiment functions in pursuit of the maximum value of road surface frictional force. Therefore, when the road surface has no peak of road surface friction coefficient relative to slip ratio, as represented by curve C2 in FIG. 1, it may happen that ultimately a state of complete lock (slip ratio S=1) occurs to frustrate the object of an antilock brake.

(2) The road surface friction coefficient is the relative value of road surface frictional force to the vertical load acting on the wheel. However, since the vertical load which acts on the wheels during the running of the vehicle is not necessarily constant, the relation between road surface friction coefficient and road surface frictional force is not exactly proportional but merely approximately so. Therefore, it does not necessarily hold true that the antilock braking device of the above embodiment which pursues the maximum value of road surface frictional force pursues the peak point P1 on the curve C1 shown in FIG. 1. The antilock braking device described in Japanese laid-open Patent Application No. 25169/1988, which controls the braking action with reference to the brake torque of the wheel, has a similar disadvantage.

(3) The above surface frictional force increases as the brake fluid pressure is increased. However, as moments of inertia around the axle exist in the wheel, there is a delay in the increases in slip ratio and road surface frictional force that follow the increasing brake fluid pressure. Therefore, when the point of braking action makes an ingress beyond and into the segment to the right of P1 on the curve C1 of FIG. 1 and the road surface friction coefficient (and the road surface frictional force, too, if the vertical load is constant) begins to decline, the brake fluid pressure may have reached an excessively high level. Therefore, even if a decline in road surface frictional force is detected at this time-point and the brake fluid pressure is accordingly relieved, it is not certain that the slip ratio immediately begins to decrease and the point of braking action reapproaches P1 from the right-hand side with a consequent upward turn of road surface frictional force. In other words, in the antilock braking device of the above embodiment in which the forthcoming decompression or compression of brake fluid is predicated on the increase or decrease in road surface frictional force in response to a fall-off of brake fluid pressure, it may happen that a complete lock occurs without a reapproach of the point of braking action to P1 from its right-hand side on the curve C1.

(4) Because of the absence of a means for sensing the stationary state of the vehicle, the unnecessary antilock braking action may continue to occur even after the vehicle has come to a stop.

An antilock braking device according to another embodiment of this invention, which has overcome the above-mentioned drawbacks, is described hereinafter with reference to FIGS. 4 through 8.

A control means 103 controls the brake fluid pressure with reference to measured values of brake pedal-depressing force, road surface friction coefficient $\mu$, chassis speed detection signal and brake fluid pressure. A brake pedal-depressing force sensor 102, brake fluid pressure generator 104, brake fluid pressure sensor 107 and brake means 105 may all be implemented by utilizing the known technologies. The road surface friction coefficient and chassis speed detection signal are obtained from a road surface friction coefficient detector 101 and a chassis speed sensor 106, both of which are described hereinafter in detail.

Like the above-mentioned control means 3 shown in FIG. 2, the control means 103 comprises electronic circuitry including a microprocessor, a memory and an input-output interface, and functions according to a program written into the memory. An example of the action of this control means 103 is shown in the flow charts of FIGS. 5 through 8.

As the brake pedal-depressing force reaches a set value, the antilock braking device of this embodiment starts functioning to make a transition from the ordinary braking action to the antilock braking action. Referring to the main routine shown in FIG. 5, step 110 represents the beginning of this antilock braking action. Subsequently at step 111, the road surface friction coefficient $\mu$ is detected and at step 112, this value of $\mu$ is stored in the variable $\mu_{t-1}$. At step 113, this value is stored in the variable $\mu_p$. Then, the brake fluid pressure is increased at step 115 and the value of $\mu$ is detected at step 116. At step 117, the value of $\mu$ detected at step 116 is stored in the variable $\mu_t$. The sequence proceeds to step 118, where the difference $\mu_t - \mu_{t-1}$ between the two stored values $\mu_t$ and $\mu_{t-1}$ is compared with a predetermined reference value $\mu_c$. If the difference $\mu_t - \mu_{t-1}$ is larger than $\mu_c$, the sequence proceeds to step 119. If that difference is either equal to or smaller than $\mu_c$, the sequence proceeds to the brake fluid decompression routine at step 123. At step 119, the value stored in the variable $\mu_t$ is stored in the variable $\mu_{t-1}$ and the stored value $\mu_{t-1}$ is updated. The sequence then returns to step 113.

Figure 6:
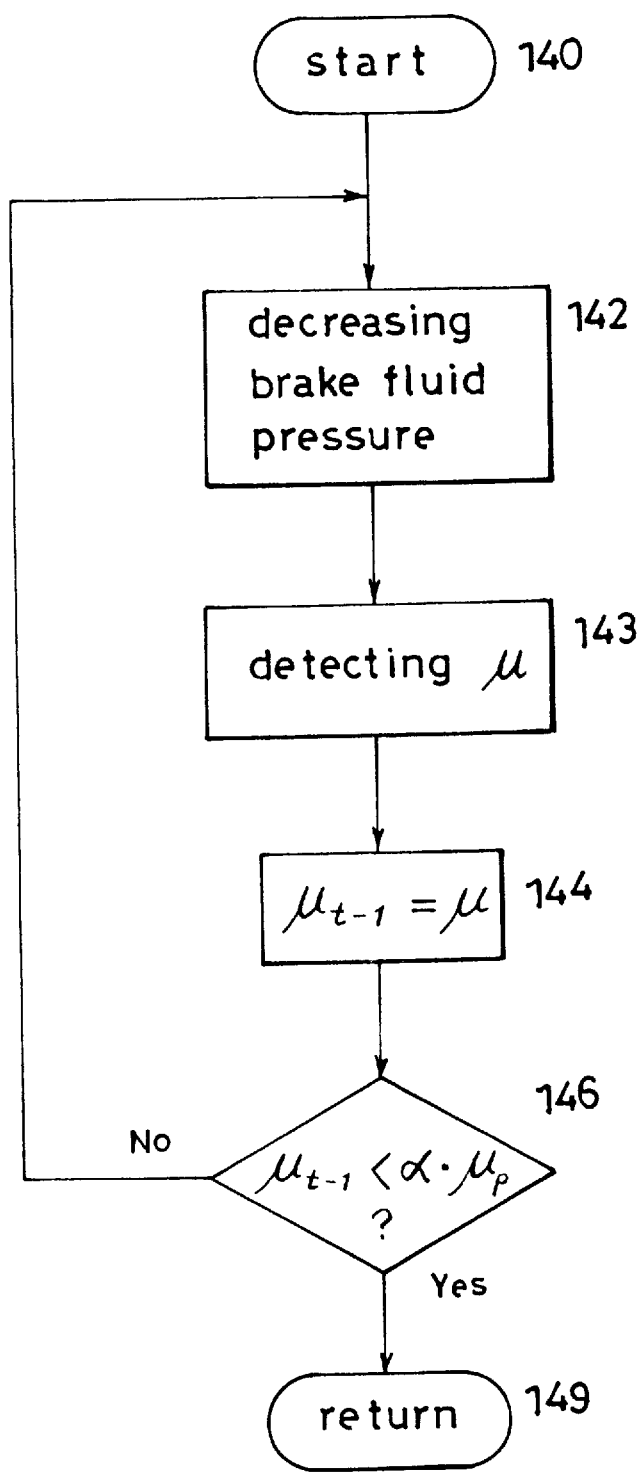
FIG. 6 is a flow chart showing the brake fluid decompression routine of FIG. 5 in detail.

In the brake fluid decompression routine 123, as illustrated in FIG. 6 the brake fluid pressure is either released or decreased to a given low level at step 142. Then, $\mu$ is detected at step 143 and this detected value is stored in the variable $\mu_{t-1}$ at step 144. The sequence then proceeds to step 146 where $\mu_{t-1}$ is compared with $\alpha \cdot \mu_p$. The coefficient $\alpha$ is a preset appropriate constant within the range of 0 to 1. If the variable $\mu_{t-1}$ is smaller, the sequence proceeds to step 149 to terminate the brake fluid decompression routine 123 and, then, to the brake fluid recompression routine at step 124. If the variable $\mu_{t-1}$ is larger or equal, the sequence returns to step 142.

Figure 7:
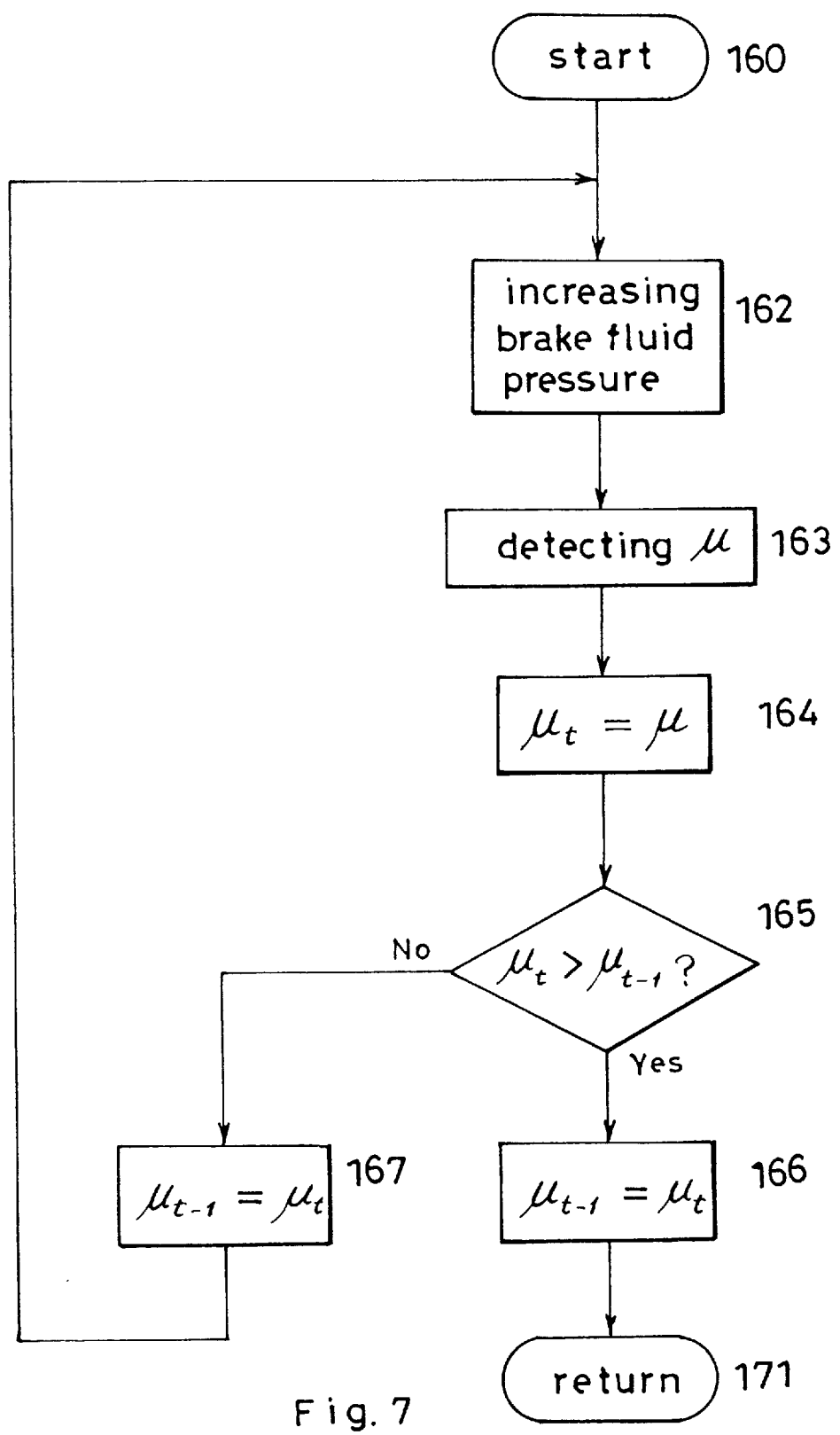
FIG. 7 is a flow chart showing the brake fluid recompression routine of FIG. 5 in detail.

In the brake fluid recompression routine 124 following the brake fluid decompression routine 123, the operation illustrated in FIG. 7 is executed. First, at step 162, the brake fluid pressure is increased. Then, $\mu$ is detected at step 163 and this value is stored in the variable $\mu_t$ at step 164. Thereafter, at step 165, the variable $\mu_t$ is compared with the variable $\mu_{t-1}$. If the variable $\mu_t$ is larger, the sequence proceeds to step 166 where the value of variable $\mu_t$ is stored in the variable $\mu_{t-1}$ to update the stored value of variable $\mu_{t-1}$. Then, the sequence proceeds to step 171 to terminate the brake fluid recompression routine and returns to the main routine at step 113. If the variable $\mu_t$ is found to be either smaller or equal at step 165, the sequence proceeds to step 167 where, as at step 166, the value of variable $\mu_{t-1}$ is updated to the value of $\mu_t$. The sequence then returns to step 162.

As the control means 103 executes the above program, the antilock braking device according to this embodiment functions as follows. After the beginning of operation of the antilock braking device, the brake fluid pressure is increased while the rising velocity of road surface friction coefficient continues to exceed a predetermined reference value. As the rising velocity of gain of road surface friction coefficient $\mu$ drops below the reference value, the brake fluid pressure is relieved or released. At this stage, the value of road surface friction coefficient $\mu$ immediately prior to the beginning of decline is memorized. This memorized value is referred to as $\mu_p$. When the road surface friction coefficient $\mu$ has declined to a predetermined percentage, for example 50%, which is dependent on $\alpha$, the brake fluid pressure is caused to increase again. Thereafter, the above sequence of operation is repeated.

Figure 4:
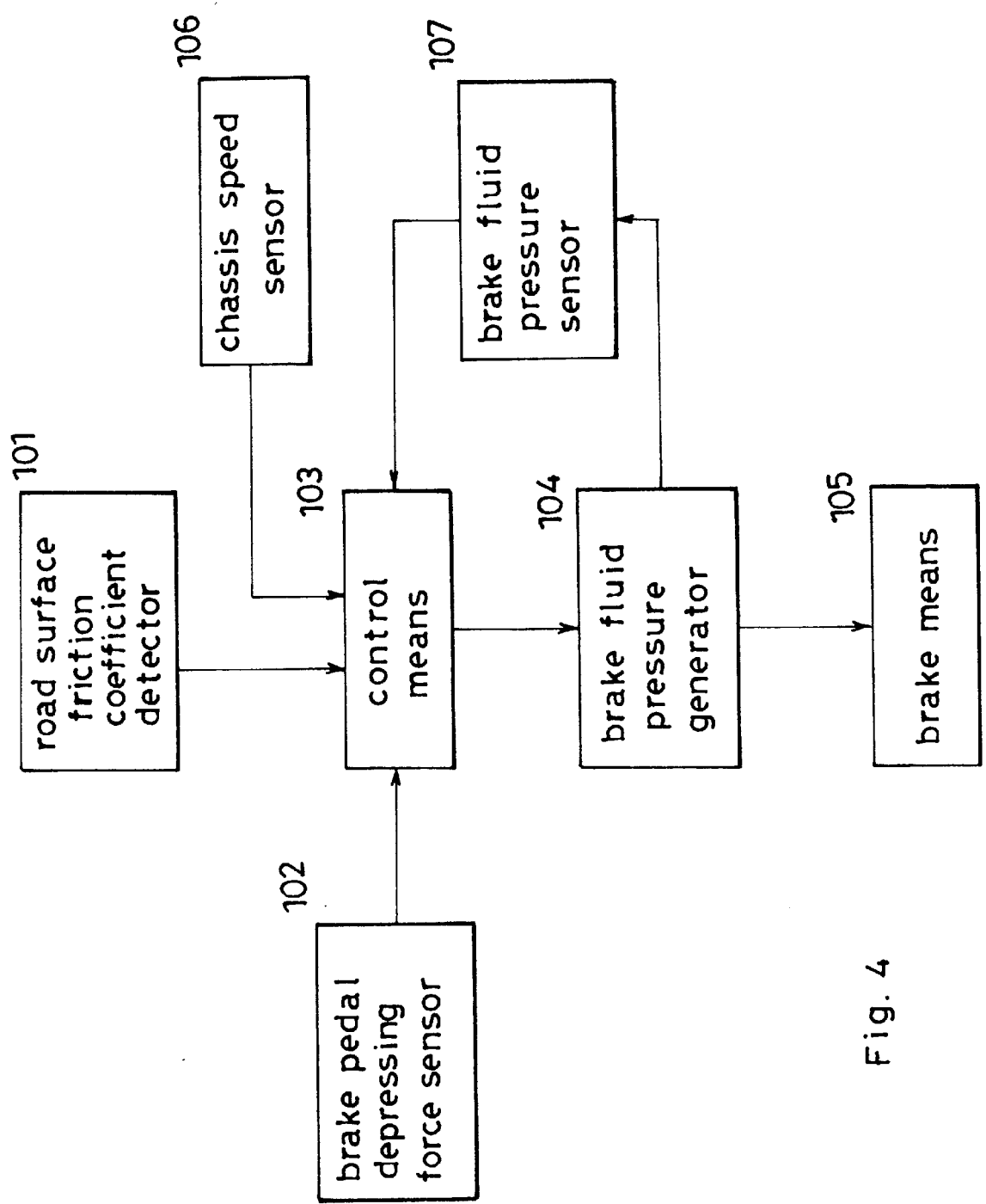
FIG. 4 is a block diagram of the antilock braking device according to another embodiment of this invention.
Figure 5:
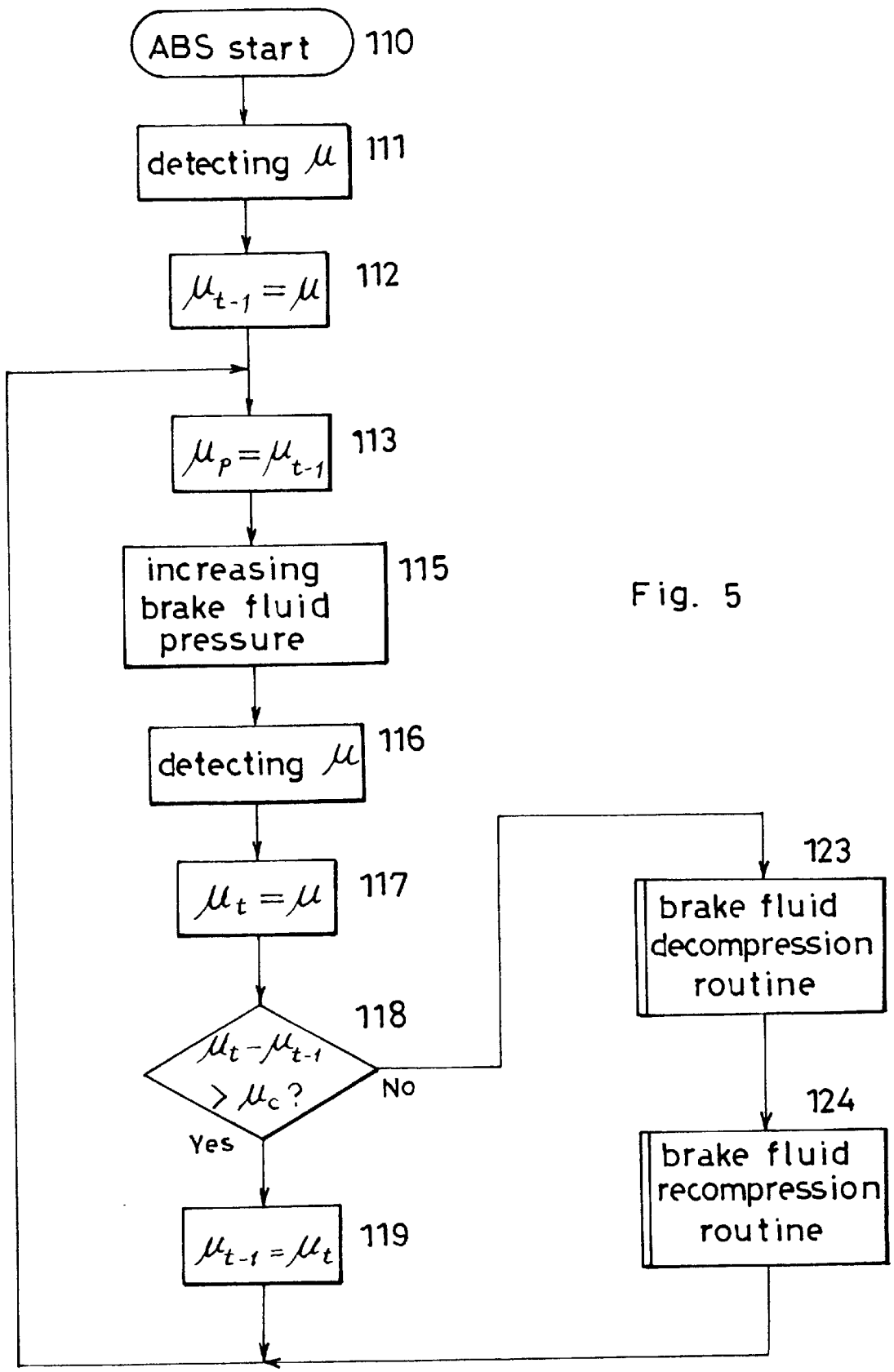
FIG. 5 is a flow chart showing the execution of the main routine in the control means built into the antilock braking device illustrated in FIG. 4.

The chassis speed sensor 106 illustrated in FIG. 4 may be the conventional device adapted for installation at the front of the driver's seat. The chassis speed can be found by electrical processing of, for example, a sensor output of the rotational speed of the change-speed drive shaft. There is usually a time lag between the rotational speed of the drive shaft and the chassis speed indication value. The detected chassis speed value carrying this time lag may be utilized as it is. As an alternative, the sensor of the change-speed drive shaft speed may be provided with a signal processing system adapted to output an appropriate chassis speed delay signal to cause a delay in the chassis speed signal output and this value be fed to the control means 103 as chassis speed data. When this chassis speed falls below a predetermined value (for example, several kilometers per hour), the control means 103 is not caused to make a transition from ordinary braking action to antilock braking action even if the brake pedal is depressed with a force over a predetermined value. When the chassis speed drops below said predetermined value during an antilock braking action, irrespective of the stage which the control means 103 is executing in the flow charts illustrated in FIGS. 5 through 7, it immediately executes the interruption routine shown in FIG. 8 to terminate the antilock braking action and controls the brake fluid system so that the ordinary braking action resumes. If the chassis speed is very low, the need for antilock braking action is not great and this action is not required at all when the vehicle is standing still. In consideration of the above, this embodiment is so designed that the antilock braking action will not take place when the chassis speed is below a predetermined value. Since the chassis speed data referred to has a delay from the rotational speed of the drive shaft, there is no response to a sudden decrease in drive shaft rotational speed due to locking of the drive wheels upon application of the brake. Therefore, the risk of a failure to enter into an antilock braking action due to locking prior to the transition from ordinary braking to antilock braking on depression of the brake pedal is reduced. Furthermore, the risk of release of the antilock braking action and return to the ordinary braking action in the event of locking during antilock braking is eliminated.

Figure 8:
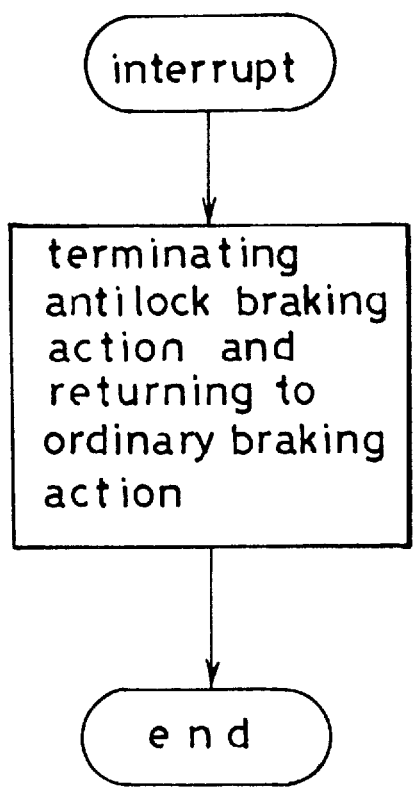
FIG. 8 is a flow chart showing an interruption of the main routine shown in FIG. 5.

Irrespective of the stage of the flow chart which the control means 103 is executing, the interruption routine shown in FIG. 8 is executed immediately upon generation of an antilock brake release instruction signal to terminate the antilock braking action and the ordinary braking action resumes. This action can be incorporated in the first-mentioned embodiment illustrated in FIGS. 2 and 3. The generation timing of the antilock braking release instruction may for example be (1) when the brake pedal-depressing force has decreased below a predetermined reference value, (2) when the brake pedal is re-depressed after releasing of the depressing force, or (3) when the engine key is turned off. Of these alternatives, (2) and (3) are advantageous in that even if an accident disenables the driver from manipulating the controls, the vehicle can be automatically brought to standstill with the ideal braking characteristic.

A more effective antilock brake control can be implemented by replacing the comparison at step 165 in the brake fluid recompression routine 124 with a comparison of whether the relation of $\mu_t - \mu_{t-1} > \mu_{c2}$, where $\mu_{c2}$ is a predetermined appropriate positive reference value, holds true. This reference value $\mu_{c2}$ preferably satisfies the condition $\mu_{C2}/\Delta t_2 > \mu_c/\Delta t_1$, wherein $\Delta t_2$ is the larger of the values of the time period in which the sequence proceeds from step 143 to step 146 and to step 149 in the brake fluid decompression routine 123 and further to step 160 to step 163 in the brake fluid recompression routine 124 and the time period of the loop in which the sequence proceeds from step 163 in the brake fluid recompression routine 124 and returns through steps 165, 167 and 162 back to step 163, and $\Delta t_1$ is the time period of the loop in which the sequence proceeds from step 116 in the main routine through steps 118, 119 and 113 and back to step 116. It is also preferable that the above-mentioned brake recompression routine be interposed downstream of step 112 in the above-mentioned main routine shown in FIG. 5. The course of return from step 119 to step 113 remains unchanged. In the above case, the reference value $\mu_{c2}$ in the brake fluid recompression routine 124 may be an appropriate value satisfying the relation $\mu_{c2}/\Delta t_2 > \mu_c/\Delta t_1$, wherein $\Delta t_2$ is the larger of the values of the time period in which the sequence proceeds from step 111 to step 163 in the interposed brake fluid recompression routine 124 and the time period of the loop in which the sequence proceeds from step 163 in the inserted brake fluid recompression routine through steps 165, 167 and 162 back to step 163.

Now, the road surface friction coefficient detector 101 embodying the principle of this invention is described below with reference to FIGS. 9 through 19.

In this embodiment, the strain on vehicle structures in the vicinity of the axle is measured by means of strain gauges 41 to 44 and 51 to 54 for the rear wheels and strain gauges 71 to 74, 75 to 78, 81 to 84 and 85 to 88 or strain gauges 41 to 44 and 51 to 54, for the front wheels, whereby the road surface frictional force and the load in the vertical direction are detected. The strain gauge itself is a known technology utilizing the fact that the electric resistance of a resistance wire changes in proportion with strain. Typically, it comprises a rectangular film in which a resistance wire has been embedded and detects the tensile strain and compressive strain in its longitudinal direction.

Figure 9:
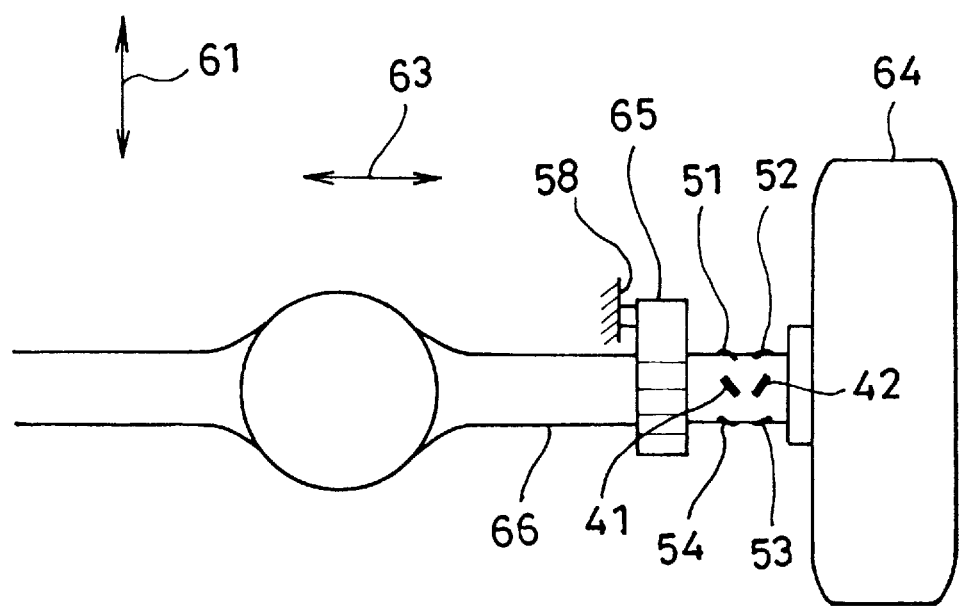
FIG. 9 is a front view showing the position of installation of strain gauges constituting the road surface friction coefficient detector embodying the principle of this invention for a vehicle structure in the vicinity of the rear wheel.
Figure 10:
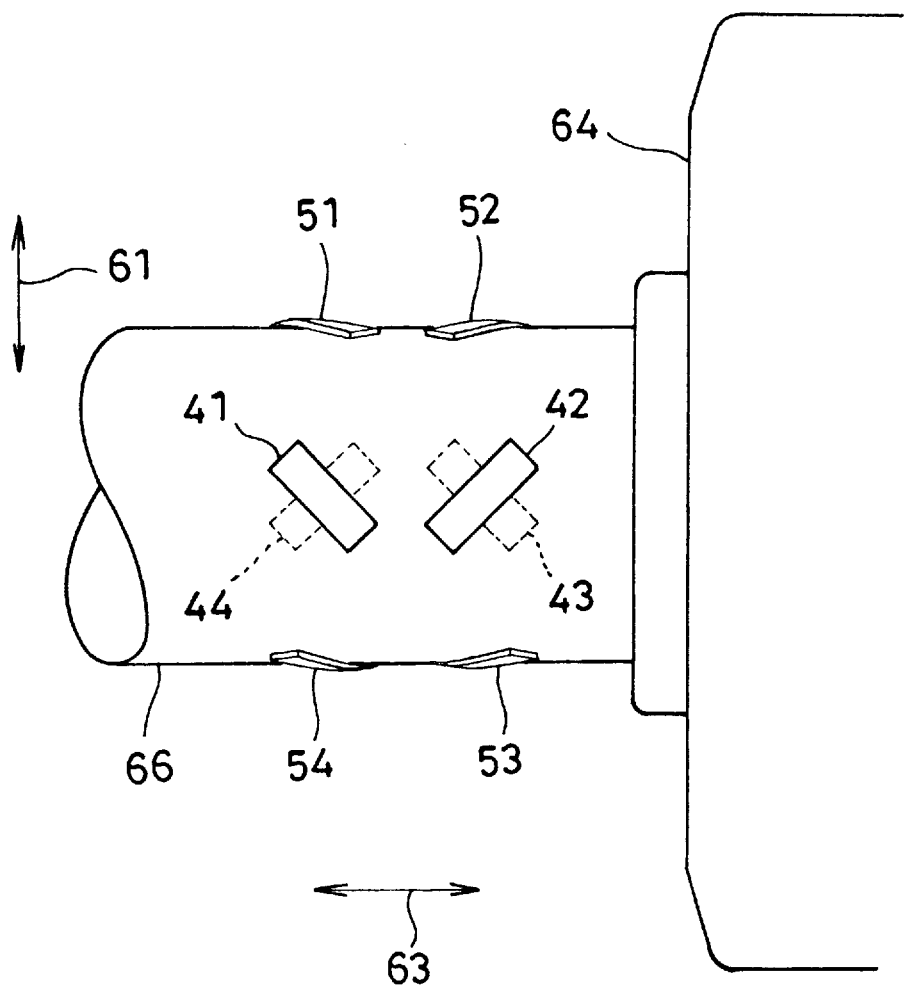
FIG. 10 is a front view, on exaggerated scale, of the position of installation of the strain gauges illustrated in FIG. 9.
Figure 11:
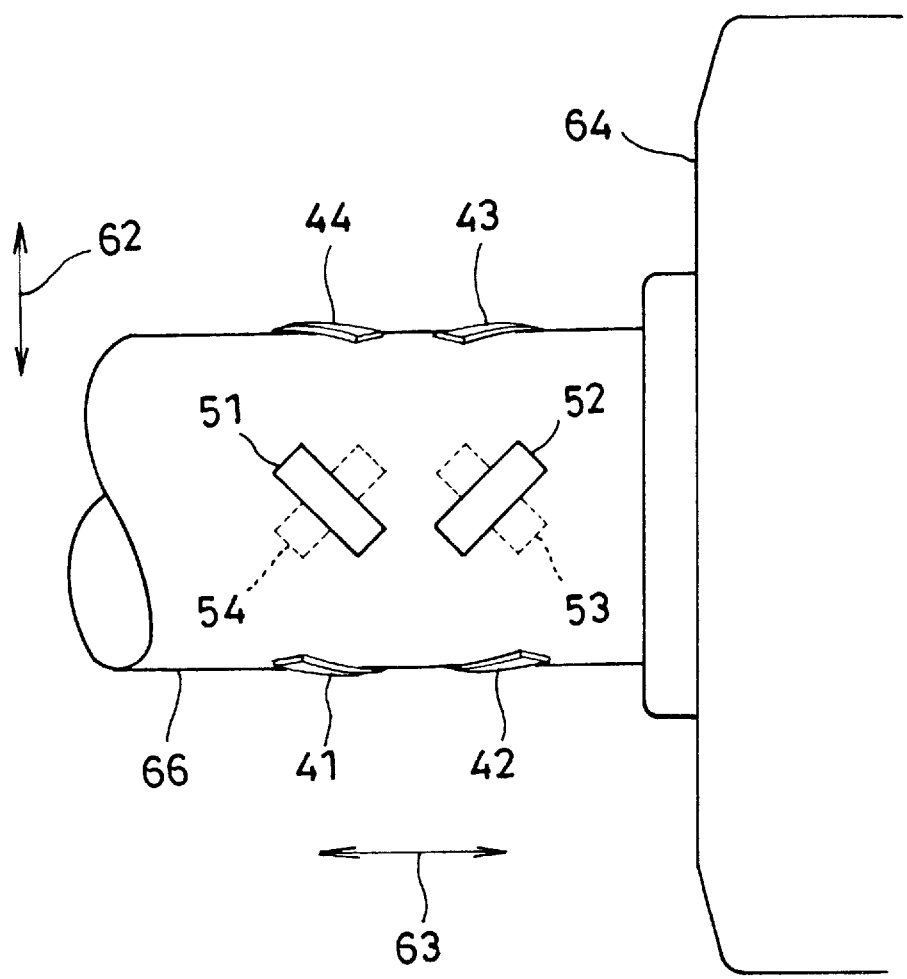
FIG. 11 is a plan view, on exaggerated scale, of the position of installation of the strain gauges illustrated in FIG. 10.
Figure 12:
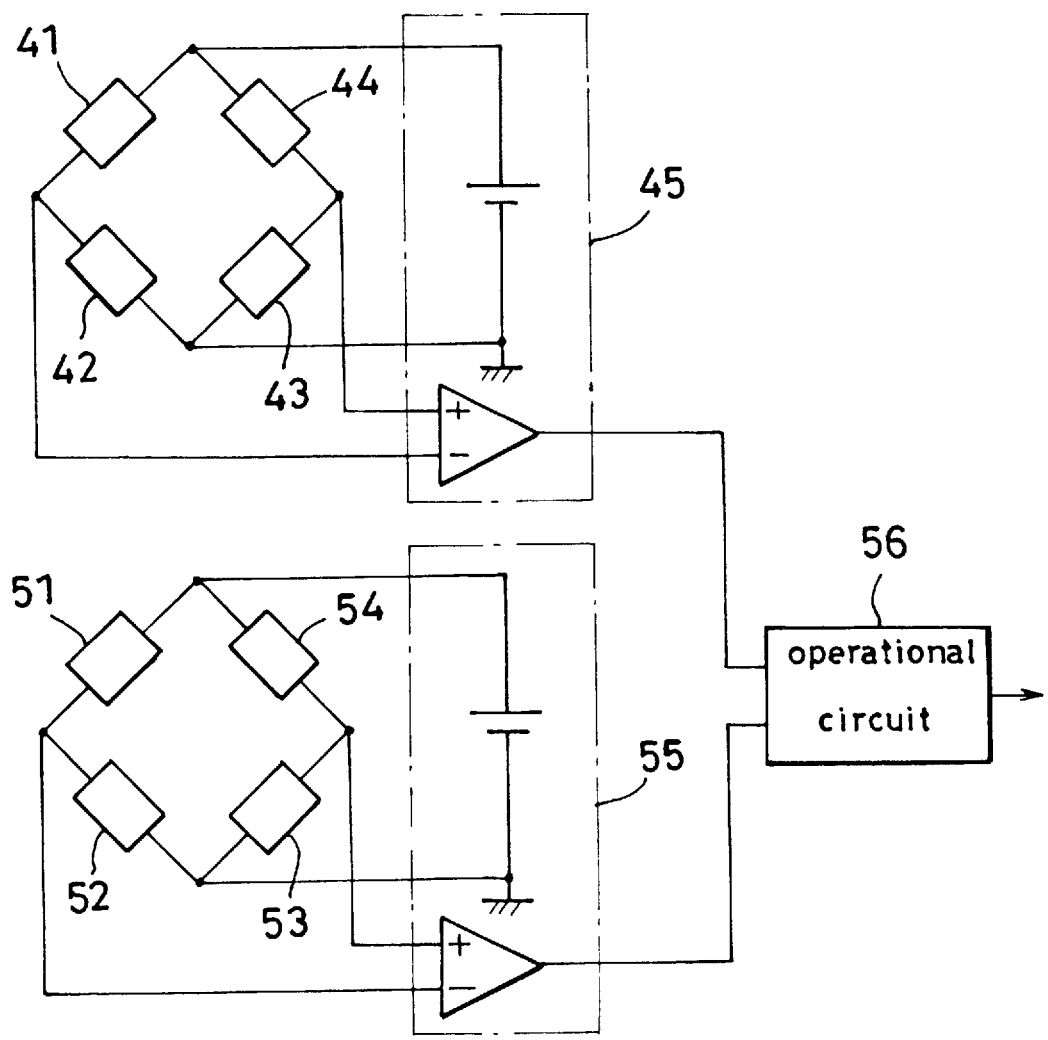
FIG. 12 is a block diagram of the road surface friction coefficient detector embodying the principle of this invention as applicable to one rear wheel.

An example of the position of attachment of strain gauges in the vicinity of a rear wheel 64 is shown in FIGS. 9 through 11. It should be understood that the arrowmarks 61, 62 and 63 indicate the vertical direction, direction of advance, and axle direction, respectively, of the wheels 64. A total of 8 strain gauges 41 to 44 and 51 to 54 are affixed to the surface of a rear axle housing 66 between the wheel 64 and a rear spring 65 secured rigidly to a car body 58. A set of 4 strain gauges 41, 42, 43 and 44 for detection of the vertical load that acts on the rear wheel 64 and another set of 4 strain gauges 51, 52, 53 and 54 for detection of the road surface frictional force which acts on the same wheel 64 are assembled into the respective bridge circuits as shown in FIG. 12 and the outputs of the respective bridge circuits are fed to amplifiers 45 and 55.

As shown in FIG. 10, the set of strain gauges 41, 42, 43 and 44 are affixed on the line of intersection of a horizontal plane including the axis or centerline of the rear axle housing 66 with the surface of the housing 66 for measuring the compressive and tensile strains in the direction at an angle of 45 degrees from the line of intersection. However, strain gauges 41 and 42 and strain gauges 43 and 44 are respectively disposed close to each other and the strain gauges 41 and 44 and the strain gauges 42 and 43 are respectively disposed in symmetric relation with respect to the centerline. The other set of strain gauges 51, 52, 53 and 54 are disposed as illustrated in FIG. 11. Thus, they are affixed on the line of intersection of a vertical plane including the centerline of rear axle housing 66 with the surface of the housing 66 for measuring the compressive and tensile strains in the direction at an angle of 45 degrees from the line of intersection. Furthermore, the strain gauges 51 and 52 and the strain gauges 53 and 54 are respectively disposed close to each other and the strain gauges 51 and 54 and the strain gauges 52 and 53 are respectively disposed in symmetric relation with respect to the centerline.

By the vertical load acting on the wheel 64, the rear axle housing 66 is subject to a bending deformation such that the centerline or axis of the housing 66 is bent on a vertical plane including the centerline. At the same time, a shearing force equivalent to the vertical load is applied vertically to the cross-sectional area perpendicular to the centerline of the rear axle housing 66. In proportion with this shearing force, a shear strain is generated in the rear axle housing 66. The bridge circuit consisting of the set of strain gauges 41, 42, 43 and 44 detects this shear strain. Thus, even if the above-mentioned bending deformation caused the respective strain gauges to undergo compression or elongation, the effects of the bending deformation on strain gauges 41, 42, 43 and 44 are mutually offset in this bridge circuit. Thus, the voltage output of the amplifier 45 is only proportional to the vertical load acting on the wheel and not subject to the effect of the moments around a rear spring 65.

The road surface frictional force acting on the wheel 64 causes a bending deformation such that the centerline of the rear axle housing 66 is bent on a horizontal plane including the centerline. At the same time, a shearing force equivalent to the road surface frictional force is applied horizontally to the cross-sectional area perpendicular to the centerline of rear axle housing 66. In proportion with this shearing force, a shear strain is generated in the rear axle housing 66. The bridge circuit consisting of strain gauges 51, 52, 53 and 54 detects this shear strain. Just as mentioned above, the effects of the bending deformation on the respective strain gauges are mutually offset in this bridge circuit. Therefore, the voltage output of the amplifier 55 is only proportional to the road surface frictional force applied to the wheel 64 and is not subject to the influence of the moments around the rear spring 65.

Furthermore, the bending deformation and shear strain due to the vertical load do not interfere with the output voltage of the bridge circuit consisting of strain gauges 51 through 54 constituting said one set, and the bending deformation and shear strain due to the road surface frictional force do not influence the output voltage of the bridge circuit consisting of strain gauges 41 through 44 constituting the other set. Though the cornering force (lateral drag) acting on the wheel 64 adds a compressive or tensile strain to the rear axle housing 66 in the direction of its centerline, these strains do not affect the output voltage of the bridge circuit consisting of strain gauges 41 through 44, nor do they interfere with the voltage output of the bridge circuit consisting of strain gauges 51 through 54.

Furthermore, as the brake is applied to the wheel 64, the brake torque (the moment about the centerline of the axle) generates a torsional deformation in the rear axle housing 66 about its axis. However, the voltage outputs of the bridge circuits consisting of the sets of strain gauges 41 to 44 and 51 to 54 are not affected by the torsional deformation.

Furthermore, in view of the fact that the rear axle housing 66 is made of a steel material with a high thermal conductivity, the temperature difference among the strain gauges 41 through 44 or among the strain gauges 51 through 54 is so small that a change in atmospheric temperature exerts little influence on the output voltages of the respective amplifiers 45 and 55. Thus, the influence of atmospheric temperature on detected vertical load and road surface frictional force values is almost negligible. If the peripheral surface of the rear axle housing 60 is locally treated with copper and the eight strain gauges are affixed to the treated area, the inter-gauge temperature gradient and, hence, the influence of atmospheric temperature will be effectively minimized.

The moments around the rear spring 65 which act on the rear axle housing 66 owing to the vertical load and road surface frictional force applied to the rear wheel 64 vary with shifting of the point of contact on the tire surface with the ground in the axle direction, even if the vertical load or road surface frictional force remains constant. Therefore, it is necessary to detect the very vertical load and road surface frictional force without picking up such moments. This embodiment meets the above demand.

As shown in FIG. 12, the road surface friction coefficient detector 101 according to this embodiment feeds to an operational circuit 56 a voltage signal proportional to the vertical load as obtainable as the output of an amplifier 45 and a voltage signal proportional to the road surface frictional force as obtainable as the output of an amplifier 55. The operational circuit 56 calculates the quotient of road surface frictional force and vertical load and outputs a voltage signal corresponding to the road surface friction coefficient $\mu$.

Figure 13:
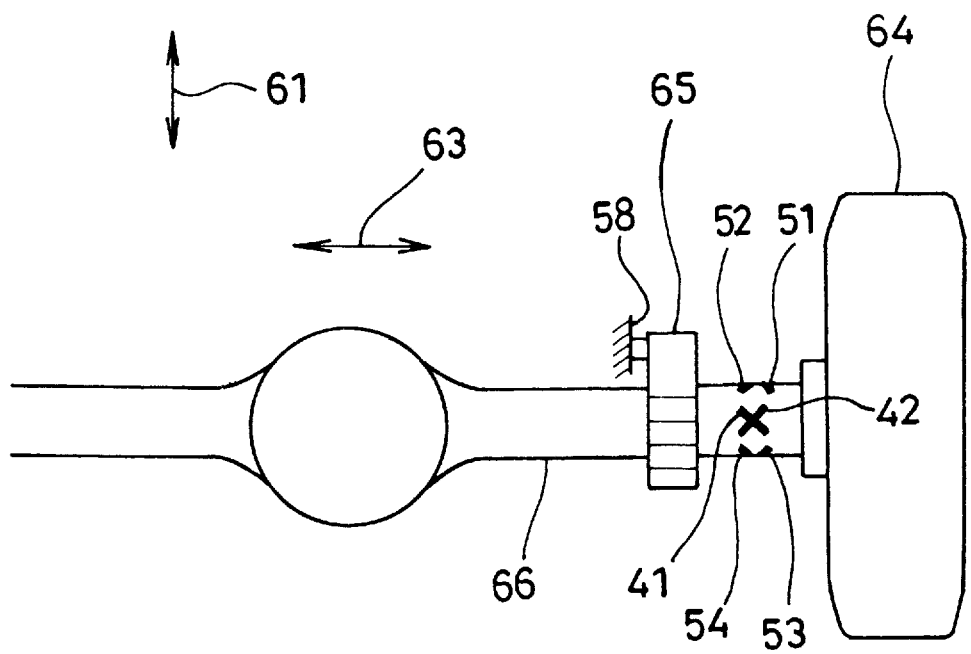
FIG. 13 is a front view showing another example of the installation of strain gauges on a vehicle structure in the vicinity of the rear wheel of a vehicle.

It should be noted that a strain gauge (tentatively called "cross gauge") which consists of two strain gauges disposed as intersecting each other at right angles and is capable of measuring the tensile or compressive strains in biaxial directions is commercially available. Therefore, as shown in FIG. 13, each of the pairs of strain gauges 41 and 42; 43 and 44; 51 and 52; and 53 and 54 may be replaced with one cross gauge to constitute bridge circuits as illustrated in FIG. 12 to accomplish the desired effect with greater efficiency. When cross gauges are used, the interval between strain gauges in each pair (for example, 41 and 42) becomes zero and the tensile or compressive strains in two perpendicular directions can be measured in one and the same position, with the result that the measurement of the vertical load and road surface frictional force can be performed with improved accuracy.

Figure 14:
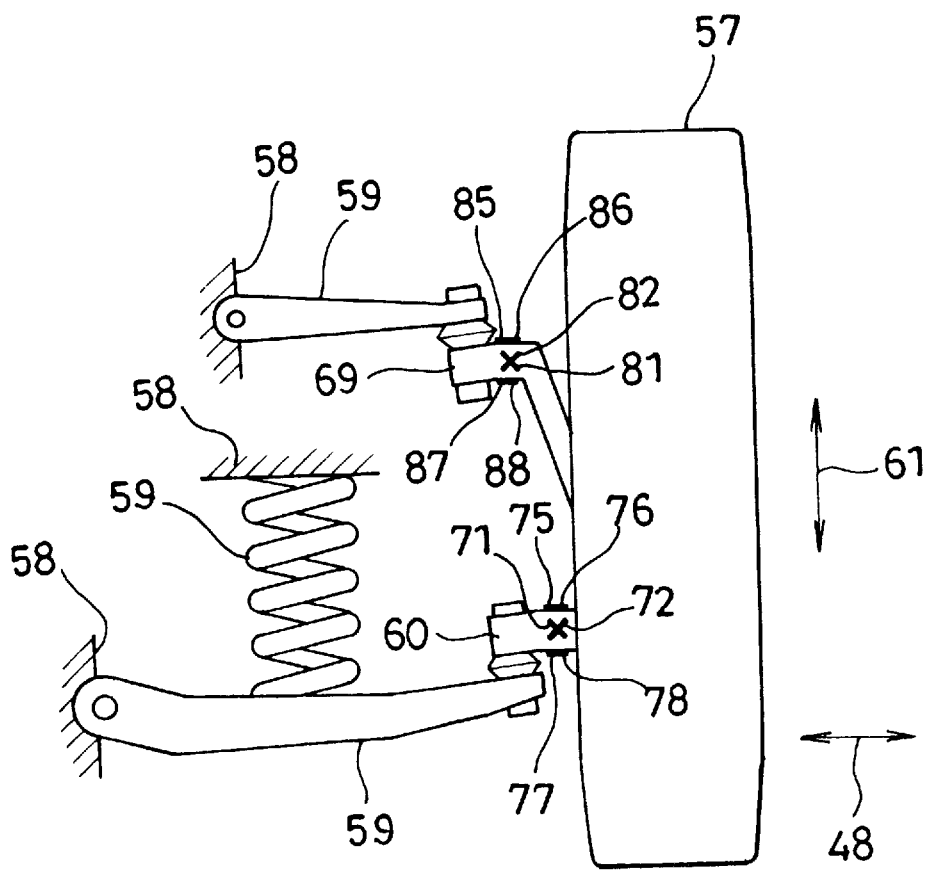
FIG. 14 is a front view showing the position of installation of strain gauges constituting the road surface friction coefficient detector embodying the principle of this invention for a vehicle structure in the vicinity of the front wheel.
Figure 15:
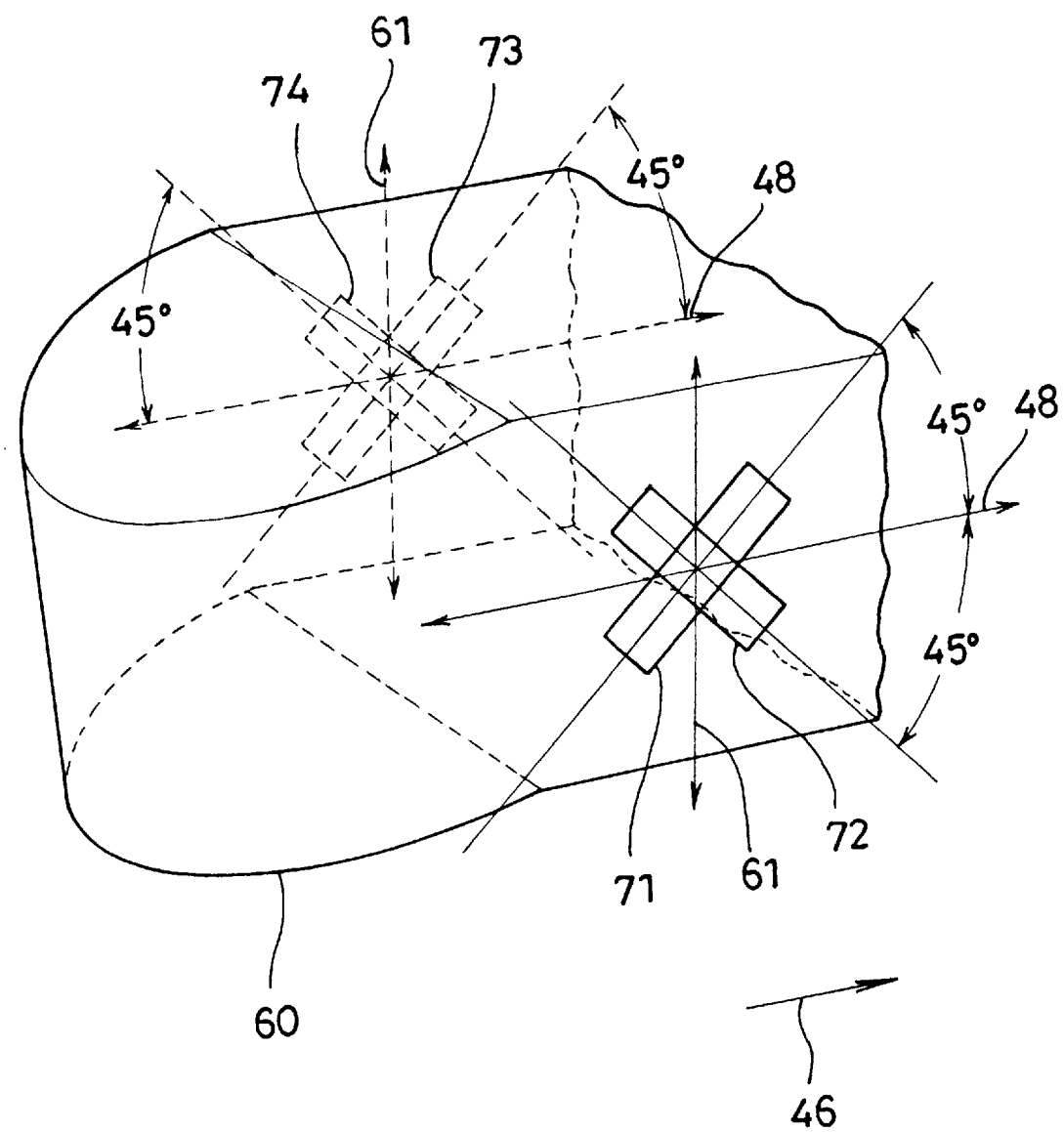
FIG. 15 is a perspective view showing, on exaggerated scale, the position of installation of the strain gauges illustrated in FIG. 14.
Figure 16:
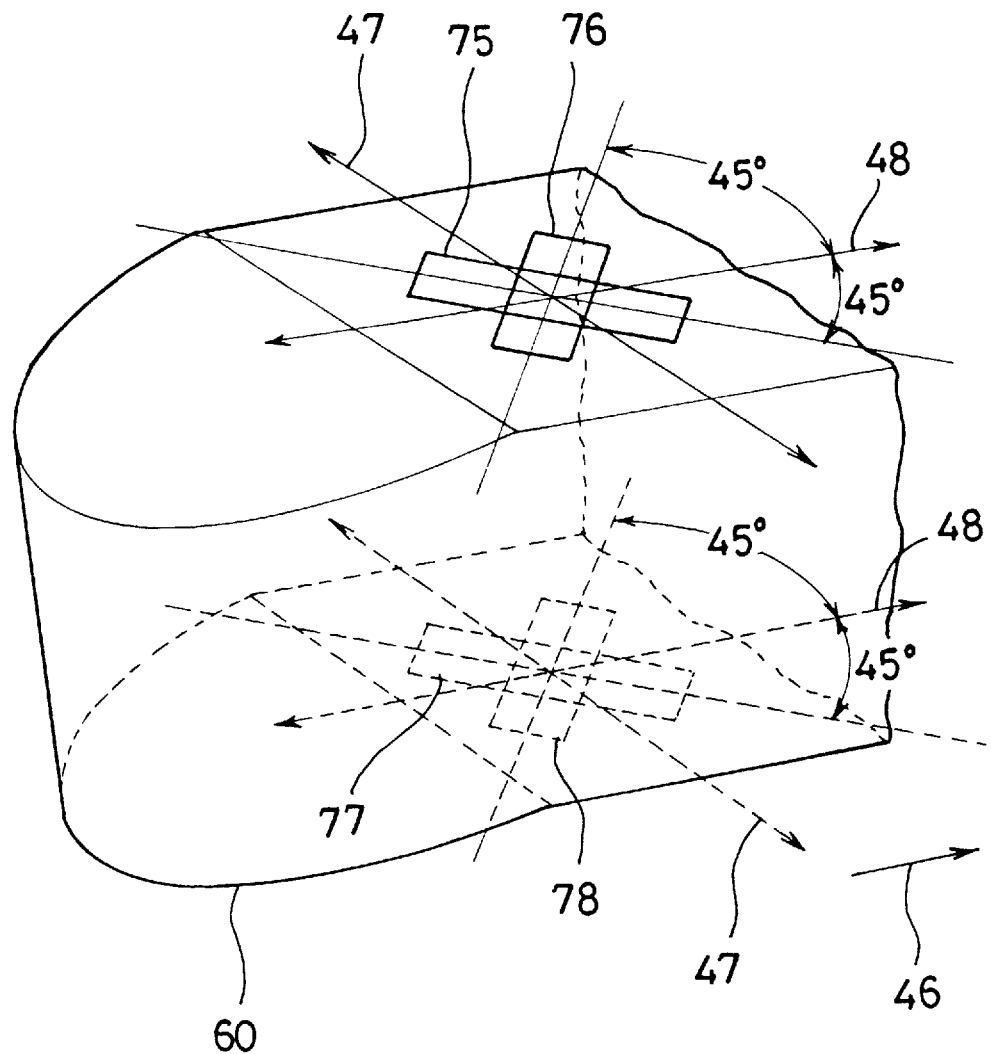
FIG. 16 is a similar perspective view showing, on exaggerated scale, the position of installation of the strain gauges illustrated in FIG. 14.

FIGS. 14 through 16 show exemplary positions of attachment of strain gauges on vehicle structures in the vicinity of the front wheel 57, taking as an example a front wheel suspension structure of the so-called wishbone type. In the views, the arrowmarks 61, 47 and 48 indicate the vertical direction, direction of advance and axle direction, respectively, of the wheel 57. The arrowmark 46 is parallel to the arrowmark 48 and points to the side on which the wheel is positioned. It is recommended that strain gauges 71 through 74 and strain gauges 81 through 84 be affixed respectively on the lateral sides of two upper and lower wheel supporting members (knuckles) 60 and 69 for transmitting the force acting on the wheel 57 to a suspension mechanism 59 connected to the vehicle body 58 and strain gauges 75 through 78 and strain gauges 85 through 88 be affixed on the top and bottom sides, respectively. In these views, the use of aforesaid cross gauges is represented.

As shown in FIG. 15, four strain gauges 71, 72, 73 and 74 constituting a set are affixed on both lateral sides of the lower wheel supporting member 60 in such a manner that the strain gauges 71 and 72 and the strain gauges 73 and 74 are respectively disposed in symmetric relation with each other on the respective lateral sides. These gauges are affixed at an angle of 45 degrees from the vertical direction 61 and the axle direction 48. Quite similarly, the strain gauges 81, 82, 83 and 84 constituting another set are affixed on both lateral sides of the upper wheel supporting member 69. The positions and direction of attachment are similar to those shown in FIG. 15 except that the supporting member 60 should read 69 and the strain gauges 71, 72, 73 and 74 read 81, 82, 83 and 84, respectively.

As illustrated in FIG. 16, strain gauges 75, 76, 77 and 78 forming another set are affixed on the top and bottom sides of the lower wheel supporting member 60 in such a manner that the strain gauges 75 and 76 and the strain gauges 77 and 78 are respectively disposed in symmetric relation on the respective sides. These gauges are affixed at an angle of 45 degrees from the direction of advance 47 and axle direction 48. Quite similarly, strain gauges 85, 86, 87 and 88 forming another set are affixed on the top and bottom sides of the upper wheel supporting member 69. The positions and direction of attachment are similar to those indicated in FIG. 16 except that the supporting member 60 should read 69 and the strain gauges 75, 76, 77 and 78 read 85, 86, 87 and 88, respectively.

Figure 17:
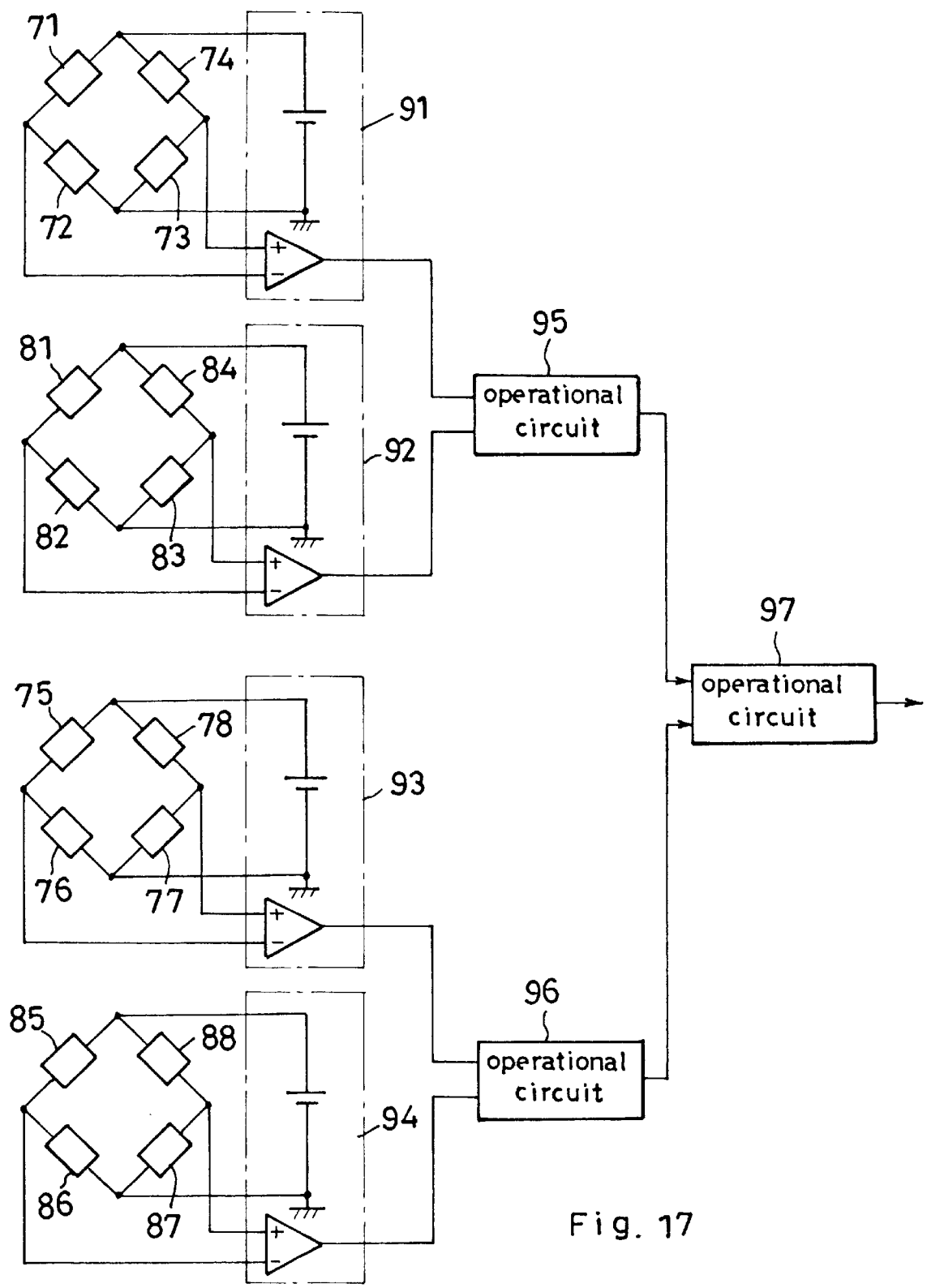
FIG. 17 is a block diagram of the road surface friction coefficient detector embodying the principle of this invention as applicable to one front wheel.

As it was the case with the rear wheel 64, each set of these strain gauges 71 through 74, 81 through 84, 75 through 78 and 85 through 88 constitutes a bridge circuit and is connected to the corresponding one of amplifiers 91, 92, 93 and 94 as shown in FIG. 17.

The vertical load acting on the wheel 57 generates a shearing force equivalent to the vertical load, as a sum of shearing forces for the upper and lower wheel supporting members 60 and 69, in vertical direction 61 in the cross-sectional area perpendicular to the axle direction 48 of each of the supporting members 60 and 69. As a result, shear strains proportional to the shearing forces acting on the supporting members 60 and 69, respectively, are generated in the respective wheel supporting members 60 and 69. The bridge circuits consisting of strain gauges 71, 72, 73 and 74 and strain gauges 81, 82, 83 and 84, respectively, detect these respective shear strains. The outputs of amplifiers 91 and 92 representing detected values of these two shear strains are added in a predetermined suitable ratio in an operational circuit 95 shown in FIG. 17 and the result is outputted. In this manner, a voltage signal proportional to the vertical load applied to the wheel 57 is obtained as the output of said operational circuit 95.

Similarly, the road surface frictional force applied to the wheel 57 generates a shearing force equivalent to the road surface frictional force, as the sum of forces for the upper and lower wheel supporting members 60 and 69, in travel direction 47 in the cross-sectional area perpendicular to the axle direction 48 of each of the wheel supporting members 60 and 69. As a result, shear strains proportional to the shearing forces acting on the supporting members 60 and 69, respectively, are generated in the wheel supporting members 60 and 69, respectively. The bridge circuits consisting of strain gauges 75, 76, 77 and 78 and strain gauges 85, 86, 87 and 88, respectively, detect these shear strains. The outputs of amplifiers 93 and 94 which represent detected values of these two shear strains are added in a predetermined suitable ratio in an operational circuit 96 shown in FIG. 17 and the result is outputted. In this manner, a voltage signal proportional to the road surface frictional force acting on the wheel 57 is obtained as the output of the operational circuit 96. The outputs of the two operational circuits 95 and 96 are fed to an operational circuit 97 which, like the operational circuit 56 shown in FIG. 12, calculates the quotient of road surface frictional force and vertical load and outputs a voltage signal corresponding to the road surface friction coefficient $\mu$.

As it is the case with the rear wheel 64, the cornering force applied to the wheel does not affect detected values of vertical load and road surface frictional force. Furthermore, the vertical load does not interfere with the detected road surface frictional force value and the reverse is also true. Moreover, for the same reason as mentioned in connection with the rear wheel 64, the influence of atmospheric temperature is also small. Similarly, too, the influence of atmospheric temperature can be further minimized by treating the surfaces of the wheel supporting members 60 and 69 with copper and affixing the strain gauges thereon. By the vertical load acting on the wheel 57, the wheel supporting members 60 and 69 are subjected not only to the above-mentioned shearing forces but also to compressive and tensile forces in the axle direction 48. However, as it is the case with the effect of cornering force, neither the detected value of road surface frictional force nor that of vertical load is influenced. Furthermore, by the braking torque acting as the brake for wheel 57 is applied, a shearing force is generated in the direction of advance 47 in the cross-sectional area perpendicular to the axle direction 48 of each of the wheel supporting members 60 and 69. As a result, shear strains proportional to the shearing forces acting on the wheel supporting members 60 and 69 are generated in the supporting members 60 and 69. The bridge circuits consisting of strain gauges 75, 76, 77 and 78 and strain gauges 85, 86, 87 and 88, respectively, detect these shear strains, respectively. However, as mentioned hereinbefore, the outputs of amplifiers 93 and 94 are added in a predetermined suitable ratio in the operational circuit 96. Therefore, the effects of shearing forces due to said torque are offset and consequently a voltage signal proportional to the road surface frictional force acting on the wheel 57 is obtained as the output of said operational circuit 96.

As will be apparent from the construction illustrated in FIG. 14, the upper wheel supporting member does not substantially bear the vertical load on the wheel. Therefore, even if the set of strain gauges 81 through 84, amplifier circuit 92 and operational circuit 95 are omitted and the output of the amplifier 91 is fed as the detected value of vertical load directly to the operational circuit 97, the error will be almost negligible.

Figure 18:
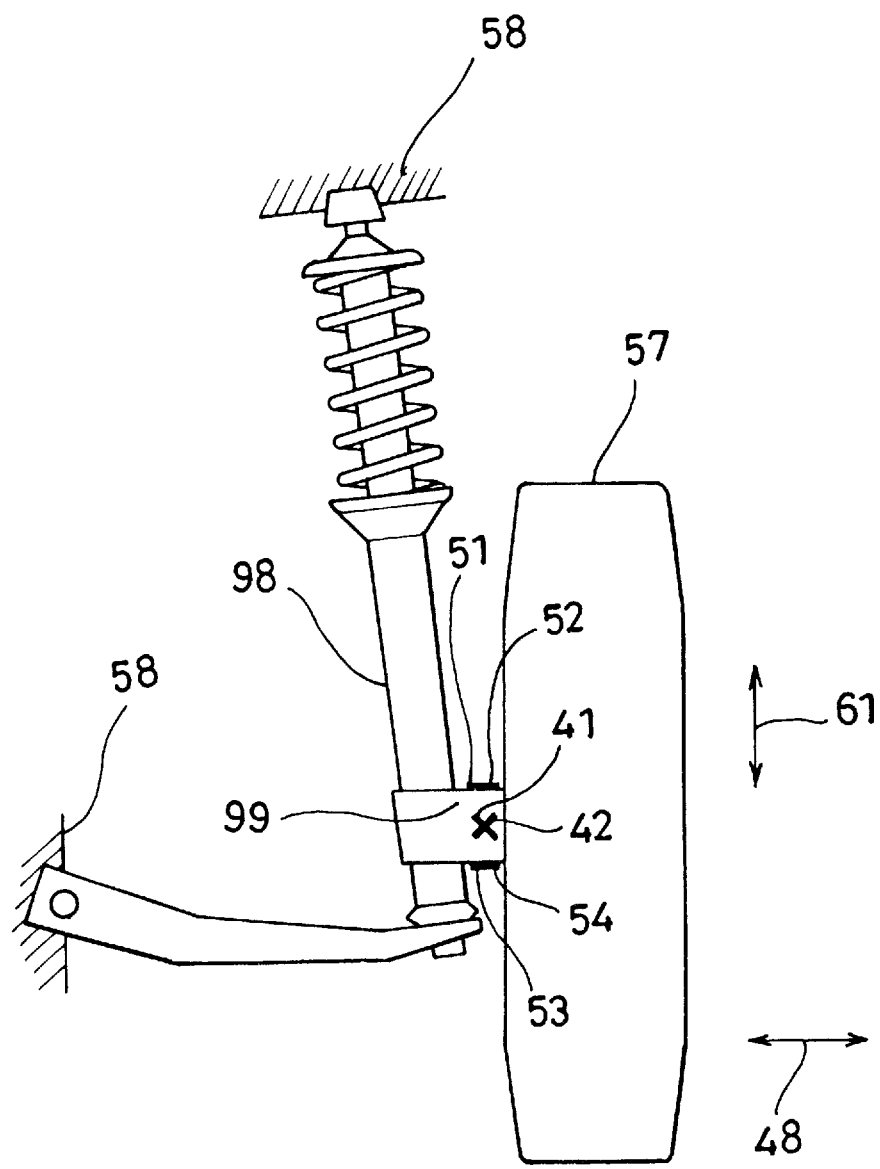
FIG. 18 is a front view showing a further example of the installation of strain gauges on a vehicle structure in the vicinity of the front wheel of a vehicle.
Figure 19:
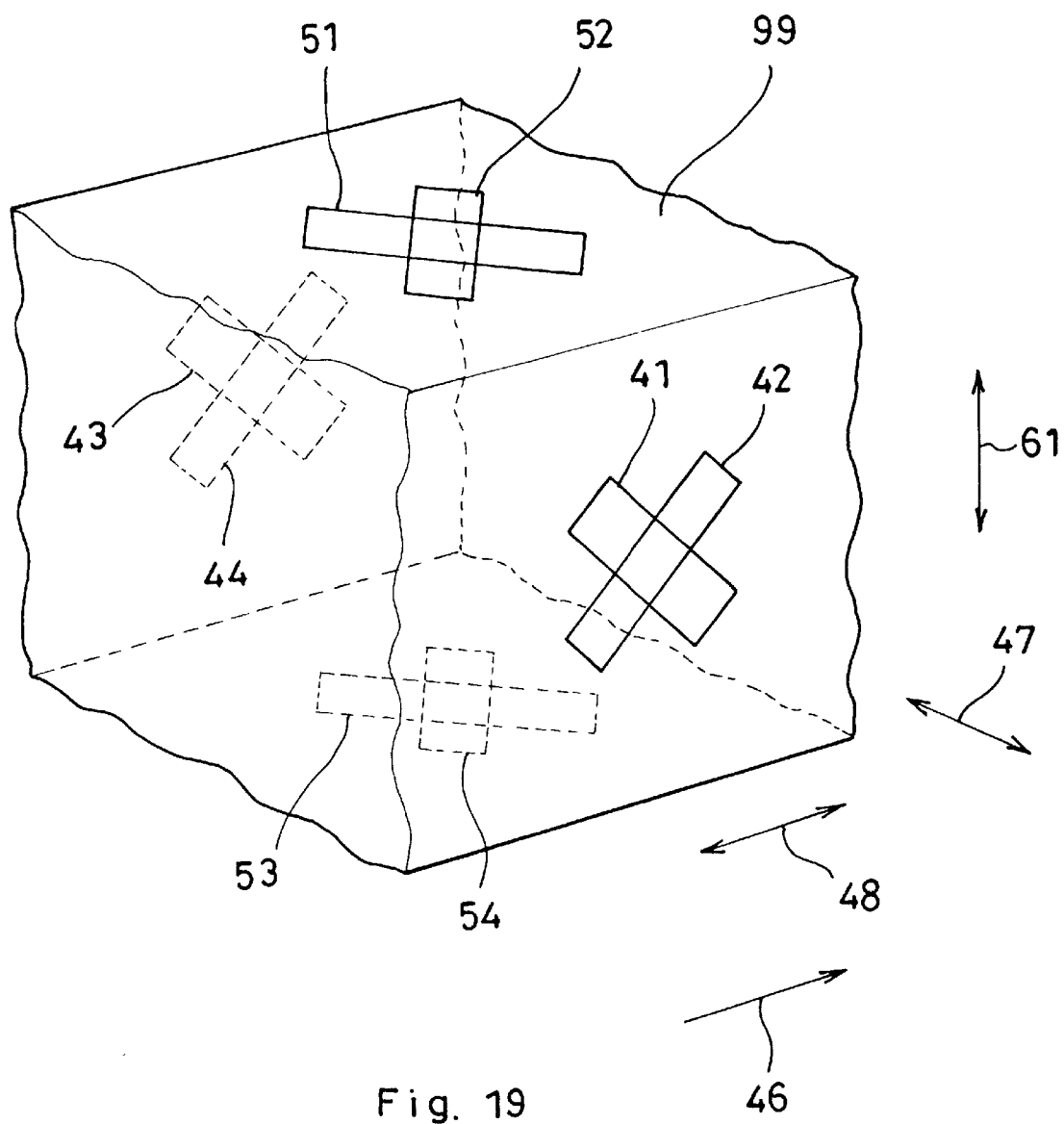
FIG. 19 is a perspective view showing, on exaggerated scale, the position of installation of the strain gauges illustrated in FIG. 18.

FIGS. 18 and 19 show the positions of installation of strain gauges on a vehicle structure in the vicinity of the front wheel 57 where the suspension mechanism is the so-called "strut" type. Preferably, strain gauges 41 through 44 are affixed on the lateral sides and strain gauges 51 through 54 on the top and bottom sides of a support member (knuckle) 99 adapted to transmit the force acting on the wheel 57 to a strut 98. In these views, the cross gauges mentioned above are shown by way of example. Like the above-mentioned strain gauges 71 through 74 or 81 through 84, the strain gauges 41 through 44 are positioned in the direction at an angle of 45 degrees with respect to vertical direction 61 and in such a manner that the pair 41 and 42 and the pair 43 and 44 are symmetrically positioned on the lateral sides of the support member 99. Similarly, the strain gauges 51 through 54 are affixed in the direction at an angle of 45 degrees with respect to the axle direction 48 and in such a manner that the pair 51 and 52 and the pair 53 and 54 are symmetrically disposed on the top and bottom sides of the support member 99. These sets of strain gauges 41 to 44 and strain gauges 51 to 54 each constitutes a bridge as illustrated in FIG. 12 and are connected to amplifiers 45 and 55, respectively. The respective amplifiers 45 and 55 output voltage signals proportional to the vertical load and road surface friction force acting on the wheel 57, respectively. These voltage signals are fed to an operational circuit 56. Just as in the case of the rear wheel 64, the operational circuit 56 outputs a voltage signal corresponding to the road surface friction coefficient $\mu$.

In this embodiment, as it is the case with the rear wheel 64 and the front wheel 57 having the "wishbone" suspension mechanism, the cornering force acting on the wheel does not interfere with the detected values of vertical load and road surface friction force. Moreover, the vertical load does not influence the detected value of road surface friction force and the reverse also holds true. Furthermore, the influence of variation in atmospheric temperature is also negligible. This influence of atmospheric temperature may be further diminished by treating the surface of the support member 99 locally with copper and affixing the strain gauges to the treated areas. In addition, just as it was the case with the rear wheel 64, the vertical load acting on the wheel 57 generates not only a shear strain but a bending deformation in the support member 99. Furthermore, when the brake is applied to the wheel 57, the brake torque superimposes a torsional deformation in the support member 99. However, neither the bending deformation nor the torsional deformation affects the voltage outputs of the bridge circuits consisting of said sets of strain gauges 41 to 44 and 51 to 54. Therefore, the amplifiers 45 and 55 each outputs a voltage signal which is exclusively proportional to the vertical load and road surface friction force acting on the wheel 57.

The road surface friction sensor 1 included in the illustration of FIG. 2 can be constituted, for the rear wheel and the front wheel connected to the strut type suspension mechanism, by the bridge circuit consisting of strain gauges 51 through 54 and amplifier 55 as shown in FIG. 12 and a voltage signal proportional to the road surface frictional force as obtainable as the output of the amplifier 55 can be directly fed to the control means 3. For the front wheel which is connected to the "wishbone" suspension mechanism, the sensor 1 can be constituted by bridge circuits comprising two sets of strain gauges 75 through 77 and 85 through 87, amplifiers 93 and 94 and an operational circuit 96 as shown in FIG. 17 and, then, a voltage signal proportional to the road surface frictional force as obtainable as the output of the amplifier 96 can be directly fed to the control means 3.

Figure 20:
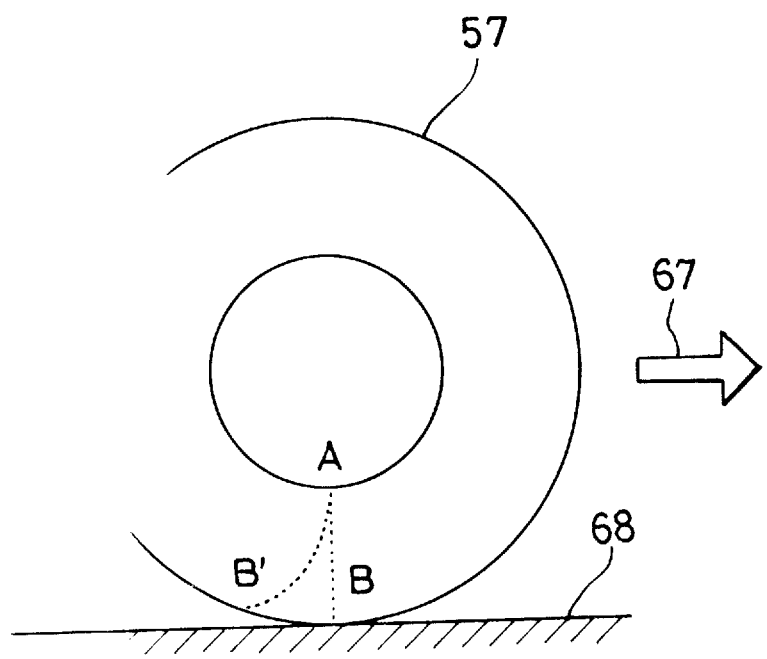
FIG. 20 is a schematic side-elevation view showing the displacement of the tire on application of the brake.

When the brake is applied to the wheel 57 during the running of the vehicle in the direction of arrowmark 67 as illustrated in FIG. 20, the centerline AB along the lateral side of the tire of this wheel 57 is displaced, for example to AB', according to the magnitude of the frictional force from a road surface 68. Moreover, the tire is deformed by the vertical load so that the distance between A and B is altered. Therefore, when the lateral side of the tire is locally marked in a suitable pattern and the deformation of the marking is measured by optical means such as image pickup elements disposed in the vicinity of the wheel 57, the strain of the tire itself can be determined through the image data. Then, based on the result, the road surface frictional force and vertical load values are calculated. Using the road surface friction coefficient $\mu$ obtained by computation from the two calculated values, the antilock braking action shown in FIGS. 5 through 8 is effected. It is also possible to calculate the road surface frictional force only and perform the antilock braking action of FIG. 3 according to the result of the calculation.

What is claimed is:

1. A road surface friction sensor comprising two sets of two strain gauges, the strain gauges of each of the sets intersecting each other on a structure of a vehicle in the vicinity of a wheel of the vehicle, the four strain gauges constituting a bridge circuit for detecting a shear strain occurring on said structure, detection signals being outputted from said bridge circuit proportional to road surface frictional force.

2. A road surface friction sensor according to claim 1 wherein said structure is an axle housing.

3. A road surface friction coefficient detector consisting essentially of a road surface friction sensor and a vertical load sensor, each of said sensors comprising two sets of two strain gauges, the strain gauges of each of the sets intersecting each other on a structure of a vehicle in the vicinity of a wheel of the vehicle, the four strain gauges of each of the sensors constituting a respective one of two bridge circuits for detecting a shear strain occurring on said structure, detection signals being outputted from one of said bridge circuits proportional to road surface frictional force and from the other of said bridge circuits proportional to vertical load, and means for calculating the quotient of road surface frictional force and vertical load and outputting a signal proportional to the road surface friction coefficient.

4. A road surface friction coefficient detector according to claim 3 wherein said structure is an axle housing.

\* \* \* \* \*